(12) United States Patent
Dave et al.

(10) Patent No.: US 9,861,625 B2
(45) Date of Patent: Jan. 9, 2018

(54) METHODS AND COMPOSITIONS FOR TREATING CANCER THROUGH INHIBITION OF PI3K

(71) Applicant: Duke University, Durham, NC (US)

(72) Inventors: Sandeep S. Dave, Chapel Hill, NC (US); Katherine Walsh, Durham, NC (US)

(73) Assignee: Duke University, Durham, WI (US)

( * ) Notice: Subject to any disclaimer, the term of this patent is extended or adjusted under 35 U.S.C. 154(b) by 0 days.

(21) Appl. No.: 15/106,870

(22) PCT Filed: Jan. 8, 2014

(86) PCT No.: PCT/US2014/010665
§ 371 (c)(1),
(2) Date: Jun. 21, 2016

(87) PCT Pub. No.: WO2015/105484
PCT Pub. Date: Jul. 16, 2015

(65) Prior Publication Data
US 2017/0014402 A1   Jan. 19, 2017

(51) Int. Cl.
| | |
|---|---|
| *A61K 31/4745* | (2006.01) |
| *A61K 31/00* | (2006.01) |
| *A61K 45/06* | (2006.01) |
| *G01N 33/50* | (2006.01) |
| *A61K 31/10* | (2006.01) |
| *A61K 31/496* | (2006.01) |
| *A61K 31/5377* | (2006.01) |
| *C12Q 1/68* | (2006.01) |
| *G01N 33/574* | (2006.01) |

(52) U.S. Cl.
CPC .......... *A61K 31/4745* (2013.01); *A61K 31/00* (2013.01); *A61K 31/10* (2013.01); *A61K 31/496* (2013.01); *A61K 31/5377* (2013.01); *A61K 45/06* (2013.01); *C12Q 1/6886* (2013.01); *G01N 33/5011* (2013.01); *G01N 33/57407* (2013.01); *G01N 33/57484* (2013.01); *C12Q 2600/106* (2013.01); *C12Q 2600/158* (2013.01); *G01N 2333/91205* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 2011/0144009 A1* | 6/2011 | Boss | .................... | C12N 5/0667 514/5.9 |
| 2012/0039875 A1* | 2/2012 | Yu | ............................ | C12Q 1/42 424/133.1 |

FOREIGN PATENT DOCUMENTS

| | | | | |
|---|---|---|---|---|
| WO | 2013/043232 | 3/2013 | | |
| WO | WO 2013043232 A2 * | 3/2013 | ........... | C07D 471/04 |

OTHER PUBLICATIONS

Walsh, K. et al., Clin. Cancer Res. 2013 vol. 19 pp. 1106-115.*
International Search Report and Written Opinion for Application No. PCT/US2014/010665 dated Dec. 15, 2014 (9 pages).
Zhang J, et al., "Genetic heterogeneity of diffuse large B-cell lymphoma," Proc. Acad. Sci. USA, 110(4): 1398-1403 (2013).
Walsh K., et al., P AKI Mediates Resistance to PI3K Inhibition in Lymphomas, Clin. Cancer Res., 19(5):1106-15 (2013).
Jima, D.D. et al., "Deep sequencing of the small RNA transcriptome of normal and malignant human B cells identities hundreds of novel microRNAs," Blood 116, e118-27 (2010).

* cited by examiner

*Primary Examiner* — Heidi Reese
(74) *Attorney, Agent, or Firm* — Michael Best & Friedrich LLP

(57) ABSTRACT

Provided herein are methods for treating cancer relating to inhibition of PI3K, as pharmaceutical compositions comprising a PI3K inhibitor and a PAK1 inhibitor.

23 Claims, 15 Drawing Sheets

METHODS AND COMPOSITIONS FOR TREATING CANCER THROUGH INHIBITION OF PI3K

BACKGROUND

Cancer arises in many forms from many different cellular origins, such as cells of the central nervous system, bone, breast, skin, thyroid, lung, liver, pancreas, prostate, soft tissues, and blood. But even among patients with histologically similar malignancies, researchers and clinicians have long recognized distinct heterogeneity in terms of clinical course and response to particular therapies, which has greatly complicated traditional treatment efforts. More recently, however, genetic and molecular analyses have begun to reveal the underpinnings for that heterogeneity. Through such studies, it has become clear that individual cancers classified under the same diagnostic umbrella often exhibit striking diversity in terms of their particular genetic alterations and gene expression patterns, and that those molecular differences frequently correlate with outcomes observed during treatment.

Efforts have thus begun aimed at identifying molecular traits that will predict responsiveness and/or resistance to available treatment options for a given subject. With such knowledge, a doctor attending to different patients diagnosed with nominally similar tumors could tailor individual treatment plans for those patients based on detectable molecular differences between their cancer cells—an approach often referred to as "personalized medicine." The development of robust methods for the targeted treatment of patients suffering from cancer and other disorders holds great promise for improving standard medical care.

SUMMARY OF THE INVENTION

The present disclosure provides methods for treating cancer in a subject. The methods may comprise determining a level of PAK1 expression in a sample from the subject and administering a PI3K inhibitor to the subject if the level of PAK1 expression in the sample is below a threshold for resistance to PI3K inhibition. The cancer may be a blood cancer. In some instances, the cancer may be a lymphoma, such as, for example, a B-cell lymphoma. The PI3K inhibitor may inhibit mTOR in addition to PI3K.

The disclosure also provides methods for determining resistance of a cancer to a PI3K inhibitor. The disclosed methods may comprise obtaining a sample comprising malignant tissue from a subject having the cancer, measuring a level of PAK1 expression in the sample, and reporting the level of PAK1 expression in the sample, wherein PAK1 expression above a control indicates resistance of the cancer to the PI3K inhibitor. Again, the cancer may be a blood cancer. In some cases, the blood cancer may be a lymphoma, and in some cases, the lymphoma may be a B-cell lymphoma. The method may also comprise treating the sample to create a test material and exposing that test material to a probe configured to detect PAK1 expression in the test material. The probe may comprise an antibody, and the probe may comprise a nucleic acid.

In addition, the disclosure provides methods for treating cancer in a subject that comprise determining a level of PAK1 expression in a sample from the subject and administering a PI3K inhibitor and a PAK1 inhibitor to the subject if the level of PAK1 expression in the sample is above a resistance threshold. Once again, the cancer may be a blood cancer. In some instances, the cancer may be a lymphoma, such as, for example, a B-cell lymphoma. The PI3K inhibitor may inhibit mTOR in addition to PI3K.

In other aspects, the disclosure provides additional methods for treating cancer in a subject. The methods may comprise requesting a test to determine a level of PAK1 expression in a sample from the subject and obtaining results of the test. The methods may include administering a PI3K inhibitor to the subject if the results of the test indicate that the level of PAK1 expression in the sample from the subject is below a resistance threshold. The methods may also include administering a PI3K inhibitor and a PAK1 inhibitor to the subject if the results of the test indicate that the level of PAK1 expression in the sample from the subject is above a resistance threshold.

The disclosure further provides methods for treating cancer in a subject that comprise administering to the subject a PI3K inhibitor and a PAK1 inhibitor.

In another aspect of the disclosure, the inventors provide for pharmaceutical compositions comprising a PI3K inhibitor and a PAK1 inhibitor.

BRIEF DESCRIPTION OF THE DRAWINGS

FIGS. 1A-1D demonstrate the identification of mutations to the PI3KCD gene found in primary diffuse large B-cell lymphoma tumors, as well as mutations detected in other genes related to the PI3K pathway (FIG. 1C). FIGS. 1E-1G show functional effects arising from deregulation of the PI3K pathway in DLBCL cells.

DETAILED DESCRIPTION

Figure 1:
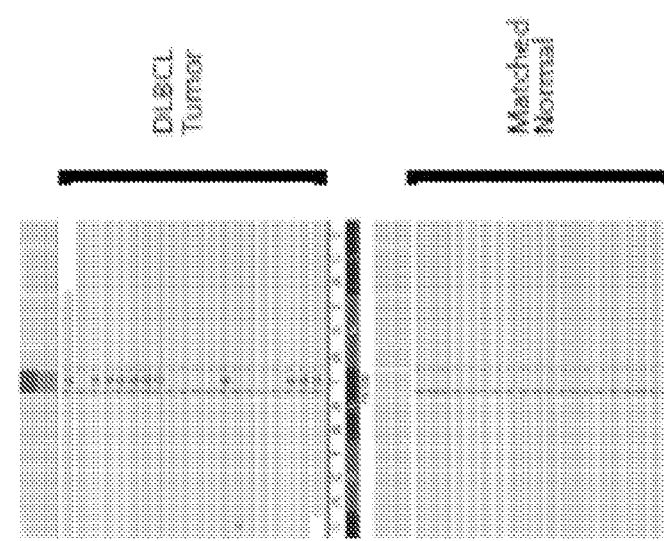
FIG. 1 illustrates deregulation of the PI3K pathway in diffuse large B-cell lymphoma (DLBCL).
Figure 1:
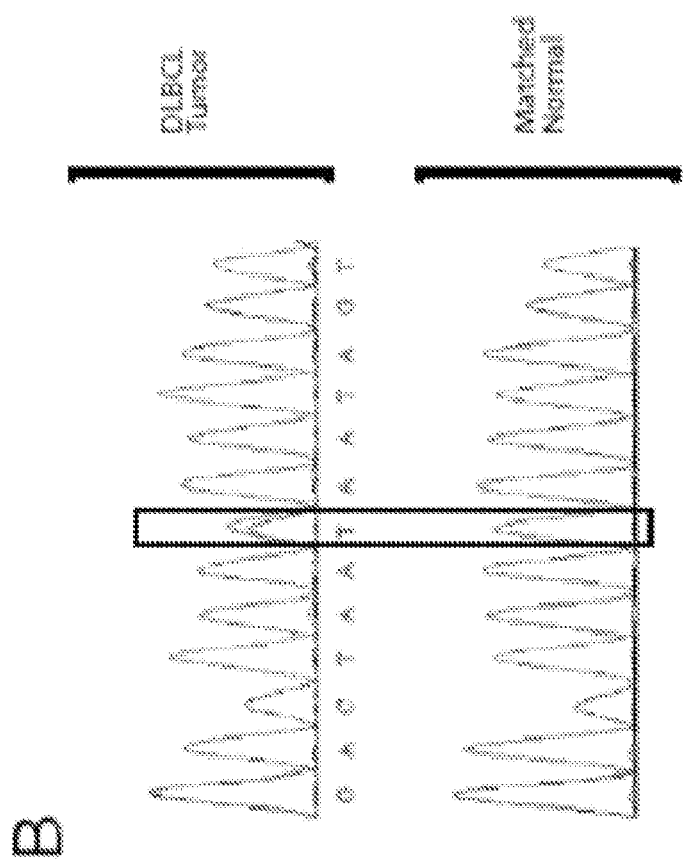
Figure 1:
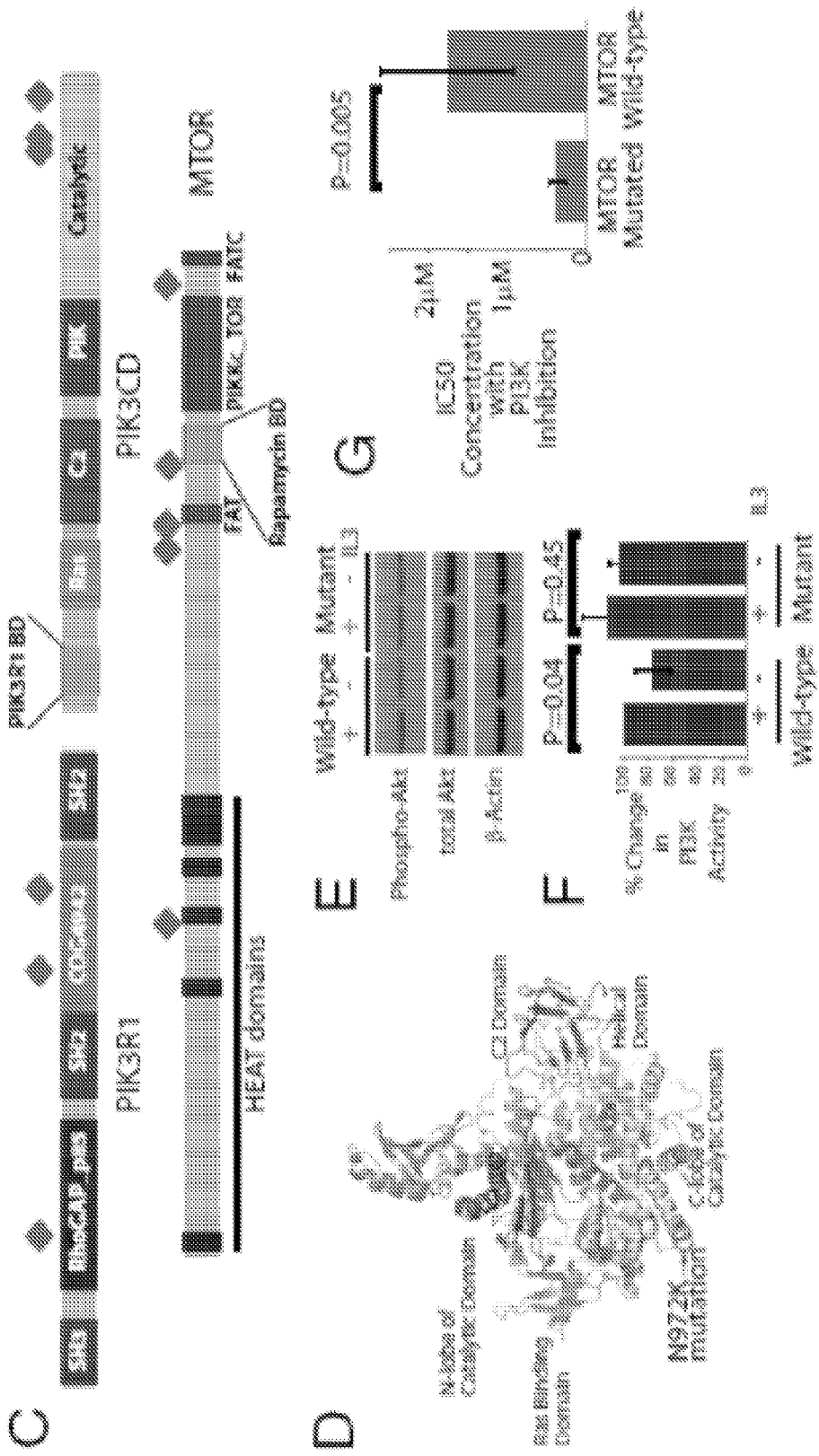

Phosphoinositide 3-kinase ("PI3K") is a key intracellular-signaling enzyme involved in a number of important signaling pathways. PI3K catalyzes the production of phosphatidylinositol triphosphates, which drive the activation of Akt protein kinases. Akt in turn modulates the activity of numerous downstream signaling proteins, including the protein kinase mTOR. When activated, PI3K signaling inhibits apoptosis and promotes cell growth, survival, and proliferation, and activation of the PI3K pathway is known to be a key oncogenic factor in a number of cancers. Accordingly, inhibitors of PI3K signaling that selectively inhibit PI3K itself or that inhibit PI3K and also directly inhibit mTOR have been evaluated for use in treating certain cancers.

The inventors have made the unexpected discovery that the expression level of protein p21-activated kinase 1 ("PAK1"), a serine/threonine protein kinase involved in intracellular signaling pathways associated with cytoskeletal reorganization and cell survival, serves as a powerful predictor of resistance to PI3K inhibition in cancer cells. Accordingly, the inventors' discovery facilitates novel and improved cancer treatment methods through determining PAK1 expression levels in individual cancers in to identify which cancers to treat with a PI3K inhibitor and which cancers are likely to resist such treatment. The methods can be carried out rapidly using nucleic acid or protein samples obtained from the cancer to be treated. In addition, the inventors have determined that inhibition of both PI3K and PAK1 through the combined or concurrent administration of PI3K and PAK1 inhibitors can overcome resistance to treatment with PI3K inhibitors alone.

Accordingly, the present invention offers critical new methods and compositions for providing informed, focused, and effective treatment based on the individual characteristics of the malignant cells in each particular subject.

1. Definitions

The terminology used herein is for the purpose of describing particular embodiments only and is not intended to be limiting. As used in the specification and the appended claims, the singular forms "a," "and," and "the" include plural references unless the context clearly dictates otherwise.

"Control" as used herein refers to a sample or condition known to exhibit a particular property of interest. In some instances, a control may include a cell line or other sample that is known to exhibit a particular property such as expression of a particular gene, expression of a particular gene in a certain measurable amount, and/or resistance to a particular drug. In some instances, a control may be a predefined property, such as, for example, expression of a particular gene in a certain measurable amount. In some instances, the particular gene may be PAK1.

Thus, as an example, and depending on the control, if a cancer is tested for the property of interest and exhibits the property in an amount that exceeds the control, that cancer may be considered to be resistant to a drug or class of drugs. As another example, depending on the control, if a cancer is tested for the property of interest and exhibits the property of interest in an amount less than the control, that cancer may be considered not to be resistant to a drug or class of drugs.

Controls may include samples such as cell lines, tissue samples, or primary cells with known PAK1 expression properties tested separately from or in parallel with a sample from a subject. Exemplary cell lines that might serve as controls, depending on the particular method, include those listed in Table 1. In other embodiments, the control may be an empirically derived threshold amount of PAK1 gene expression, such that PAK1 expression in a sample measuring above the control indicates resistance to a drug and/or such that PAK1 expression in a sample measuring below the control indicates a lack of resistance to a drug. Analyzing PAK1 expression in a sample with reference to a control may indicate resistance or the lack of resistance to a drug with a statistically defined degree of confidence, such as 60% probability, 70% probability, 80% probability, 85% probability, 90% probability, 91% probability, 92% probability, 93% probability, 94% probability, 95% probability, 96% probability, 97% probability, 98% probability, or 99% probability.

TABLE 1

| Disease/Histology | Cell Lines | Growing Conditions | BEZ235 (μM) | BKM120 (μM) | BGT226 (μM) |
|---|---|---|---|---|---|
| MantleCellLymphoma | JVM13 | RPMI 10% FBS | 0.8694 | 0.9333 | |
| MantleCellLymphoma | Rec1 | RPMI 10% FBS | 0.0823 | 0.7755 | 0.0359 |
| MantleCellLymphoma | Mino | RPMI 10% FBS | 0.0608 | 0.4603 | 0.0105 |
| MantleCellLymphoma | JVM2 | RPMI 10% FBS | 0.491 | 1.3905 | |
| MantleCellLymphoma | Jeko | RPMI 10% FBS | 0.051 | 0.7516 | 0.0166 |
| GCB DLBCL | Farage | RPMI 10% FBS | 0.5094 | 0.752 | 0.1622 |
| GCB DLBCL | BJAB | RPMI 10% FBS | 0.0269 | 1.4706 | 0.0085 |
| GCB DLBCL | LY1 | OCI | 0.0164 | 0.382 | |
| GCB DLBCL | LY2 | OCI | 0.0297 | 2.2223 | |
| GCB DLBCL | LY7 | OCI | 0.257 | 2.5487 | 0.0204 |
| GCB DLBCL | LY8 | OCI | 0.6943 | 1.3736 | |
| GCB DLBCL | LY19 | OCI | 0.2236 | 1.8869 | 0.0333 |
| GCB DLBCL | HBL2 | RPMI 10% FBS | 1.5562 | 1.4246 | |
| GCB DLBCL | HT | RPMI 10% FBS | 2.6052 | 0.4352 | |
| GCB DLBCL | Karpas422 | RPMI 10% FBS | 0.022 | 2.081 | 0.0853 |
| GCB DLBCL | Pfeiffer | RPMI 10% FBS | 0.0171 | 1.0441 | 0.0208 |
| GCB DLBCL | RCK8 | RPMI 15% FBS | 0.02 | 3.2553 | 0.0218 |
| GCB DLBCL | RL | RPMI 10% FBS | 0.026 | 2.5977 | 0.0641 |
| GCB DLBCL | Sci-1 | RPMI 10% FBS | 0.035 | 0.9853 | 0.0245 |
| GCB DLBCL | Ski | RPMI 10% FBS | 0.025 | 0.2364 | |
| GCB DLBCL | SUDHL4 | RPMI 15% FBS | 0.0608 | 1.1134 | 0.0513 |
| GCB DLBCL | SUDHL7 | RPMI 15% FBS | 0.0222 | 0.2329 | |
| GCB DLBCL | Toledo | RPMI 10% FBS | 0.0204 | 2.0058 | |
| GCB DLBCL | WSUNHL | RPMI 10% FBS | 0.0162 | 1.2561 | |
| PMBL | K1106 | RPMI 15% FBS | 0.536 | 1.8678 | 0.0182 |
| PMBL | MEDB1 | RPMI 10% FBS | 1.8317 | 7.7905 | 0.0497 |
| PMBL | U2940 | RPMI 10% FBS | 0.0354 | 4.4497 | |
| Burkitt Lymphoma | Daudi | RPMI 10% FBS | 0.0467 | 1.3029 | 0.0864 |
| Burkitt Lymphoma | CA46 | RPMI 10% FBS | 0.0284 | 0.72939 | 0.0276 |

TABLE 1-continued

| Disease/Histology | Cell Lines | Growing Conditions | BEZ235 (µM) | BKM120 (µM) | BGT226 (µM) |
|---|---|---|---|---|---|
| Burkitt Lymphoma | EB1 | RPMI 10% FBS | 0.0226 | 1.0664 | 0.0716 |
| Burkitt Lymphoma | EB2 | RPMI 10% FBS | 0.0702 | 1.07 | 0.1988 |
| Burkitt Lymphoma | EB3 | RPMI 10% FBS | 0.0368 | 0.65478 | 0.0445 |
| Burkitt Lymphoma | Jijoye | RPMI 10% FBS | 0.1402 | 2.735 | 0.0131 |
| Burkitt Lymphoma | Raji | RPMI 10% FBS | 0.3004 | 2.3149 | 0.0798 |
| Burkitt Lymphoma | Ramos | RPMI 10% FBS | 0.051 | 1.0406 | |
| Burkitt Lymphoma | Namwala | RPMI 10% FBS | 0.0321 | 0.7145 | |
| Burkitt Lymphoma | BL2 | RPMI 10% FBS | 0.0499 | 0.722 | |
| Burkitt Lymphoma | BL41 | RPMI 10% FBS | 0.01164 | 5.0311 | |
| Hodgkin Lymphoma | RMPI6666 | RPMI 10% FBS | 0.052 | 3.3042 | |
| Hodgkin Lymphoma | L1236 | RPMI 10% FBS | 0.05997 | 1.1196 | 0.0124 |
| Hodgkin Lymphoma | L428 | RPMI 10% FBS | 0.0146 | 1.8713 | |
| ABC DLBCL | LY3 | OCI | 0.08 | 0.8929 | 0.0204 |
| ABC DLBCL | HBL1 | RPMI 10% FBS | 0.0717 | 1.6721 | |
| ABC DLBCL | TMD8 | MEM-α 10% FBS | 0.1177 | 0.7645 | 0.1011 |
| ABC DLBCL | LY10 | OCI | 9.3917 | 1.5249 | |
| ABC DLBCL | Riva | RPMI 10% FBS | 0.5173 | 0.476 | |
| ABC DLBCL | U2932 | RPMI 10% FBS | 0.0961 | 5.3598 | |
| Multiple Myeloma | U266 | RPMI 15% FBS | 0.1666 | 5.5986 | |
| Multiple Myeloma | SKMM1 | RPMI 10% FBS | 0.0484 | 0.826 | |
| Multiple Myeloma | RPMI8226 | RPMI 10% FBS | 0.0569 | 0.674 | |
| Multiple Myeloma | KMS12 | RPMI 10% FBS | 0.0231 | 0.9542 | |
| Multiple Myeloma | IM9 | RPMI 10% FBS | 4.4973 | 0.57462 | 0.2006 |
| Multiple Myeloma | H929 | RPMI 10% FBS | 0.1127 | 1.2013 | 0.0036 |
| AML | U937 | RPMI 10% FBS | 0.015 | 0.8954 | 0.0112 |
| AML | KG1 | IMDM 20% FBS | 0.0799 | 0.7243 | 0.0251 |
| ALL | Reh | RPMI 10% FBS | 0.484 | 1.0249 | 0.0134 |
| ALL | SR | RPMI 10% FBS | 0.06425 | 0.8067 | |
| T-cell | Molt 4 | RPMI 10% FBS | 0.1675 | 1.1096 | 0.008 |
| T-cell | RPMI8402 | RPMI 10% FBS | 0.2205 | 1.2206 | |
| T-cell | Jurkat | RPMI 10% FBS | 0.0332 | 1.1914 | |

The control may be a sample from a subject that is cancer free, or a sample of noncancerous tissue from a subject having a cancer. The relative PAK1 expression in one or more control samples can be determined with respect to one or more expression standards. The standards can comprise, for example, the average level of PAK1 expression previously obtained for a group of normal samples or a representative group of cell lines.

"Expression," as used herein, includes processes by which a gene's genetic information is used to synthesize a functional gene product, such as a protein or an RNA present within a cell. Accordingly, the expression of a gene product can be assessed using methods that detect a protein or an RNA molecule encoded by the corresponding gene of interest. In addition, expression of a gene product in one sample can often be quantified and compared to expression of a like gene product in another sample. Exemplary means used to assess gene expression include microarray analyses, quantitative PCR, Northern blotting, in situ hybridization, Western blotting, and SAGE.

"Inhibitor" as used herein refers to any substance that at least partially blocks a function of a protein Inhibition may be observed, for example, when the substance is exposed to the protein in vitro, when the substance is exposed to cultured cells expressing the protein, or when the substance is administered to a subject. An inhibitor may selectively affect only one function of one protein, or it may affect multiple protein functions of one or more proteins. Inhibitors may include, for example, small molecules, peptides, proteins, and antibodies.

"Resistance" as used herein is a relative term that indicates a reduced susceptibility of a cancer to a particular drug or class of drugs. Thus, among a group of cancers arising from different sources and/or diagnostic categories, some may exhibit relatively higher susceptibility to a dose of a given drug (as measured by, e.g., reduced cellular proliferation, reduced cell viability, increased apoptosis, or reduced disease progression), while others may relatively lower susceptibility to the same dose of the same drug (as measured by, e.g., minimal or insignificant changes to cellular proliferation, cell viability, apoptosis, or disease progression). Those cancers exhibiting relatively unaltered functions in the presence of the drug can be said to show resistance to the drug. In addition, some cancers might require a relatively low dose exposure to a given drug to achieve a particular effect on cellular function, while other cancers might require a relatively high dose exposure to the same drug to achieve the same effect on cellular function. Those cancers requiring a relatively high dose of the drug to achieve the effect can be said to show resistance to the drug.

2. Methods for Treating a Cancer in a Subject

The herein described methods of treating cancer in a subject in need thereof permit improved treatment directed to particular properties of that subject's disease. In particular, the level of expression of PAK1 exhibited by a cancer may influence whether a PI3K inhibitor is administered to the subject or whether a PI3K inhibitor is administered with another therapeutic agent, such as a PAK1 inhibitor. The level of expression of PAK1 may be determined in a sample from the subject.

a) Subject

In the disclosed methods, the subject may be a human. The subject may be male or female, adult or juvenile. In some embodiments, the subject may be a patient already undergoing treatment for a disease, such as a cancer.

b) Cancers

Dysregulation of PI3K signaling is an oncogenic event in a number of cancers, and cancer patients may benefit from the disclosed methods. The cancer to be treated may be any cancer. Such cancers include, for example, various solid tumors as well as blood cancers like lymphomas, leukemias, and myelomas. Particular examples of such blood cancer histologies include Burkitt lymphoma, DLBCLs, follicular lymphoma, Hodgkin lymphoma, T-cell lymphoma, acute myelogenous leukemia, acute lymphoblastic leukemia, chronic myelogenous leukemia, chronic lymphoblastic leukemia, and multiple myeloma.

c) Sample

The sample may be any cell type, tissue, or bodily fluid. The sample may comprise nucleic acid, tissue or cells from the subject. The tissue or cells may be cancer tissue or cells. The sample may be used directly as obtained from the subject or following pretreatment to modify a character of the sample. Pretreatment may include extraction, concentration, inactivation of interfering components, and/or the addition of reagents.

Any cell type, tissue, or bodily fluid may be utilized to obtain the sample. Such cell types, tissues, and fluid may include sections of tissues such as biopsy and autopsy samples, frozen sections taken for histologic purposes, blood, plasma, serum, sputum, stool, tears, mucus, saliva, hair, and skin. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from the subject, but can also be accomplished by using previously isolated cells (e.g., isolated by another person, at another time, and/or for another purpose). Archival tissues, such as those having treatment or outcome history, may also be used. Nucleic acid and/or protein purification may not be necessary.

The sample from the subject may be obtained by methods such as biopsy, blood sampling, and other techniques known to one of skill in the art.

d) Measuring Expression

The sample can be tested for expression of PAK1, which may include testing the sample for the presence of PAK1 mRNA or PAK1 protein or testing to determine the amount of PAK1 mRNA or PAK1 protein in the sample on a relative or quantitative basis. Techniques for testing PAK1 expression in such a sample can include, but are not limited to, microarray analyses, quantitative RT-PCR, Northern blotting, in situ hybridization, Western blotting, and SAGE. Other methods for testing PAK1 expression may be apparent to one having ordinary skill in the art.

e) PI3K Inhibitor

The methods may include administering a PI3K inhibitor to a subject. Examples of PI3K inhibitors may include BKM120, BEX235, BGT226, Idelalisib, GDC-0941, IPI-145 (INK1197), GSK2636771, and PI-103. PI3K inhibitors may inhibit mTOR as well as PI3K; examples of such dual inhibitors include BEZ235, BGT226, VS-5584 (SB2343), PI-103, ZSTK474, and GSK1059615. The PI3K inhibitor is administered in pharmacologically acceptable compositions using suitable routes of administration and dosages as described in more detail below and as can be recognized and appreciated by one of ordinary skill in the art.

f) PAK1 Inhibitor

The methods may include administering a PAK1 inhibitor to a subject. Examples of PAK1 inhibitors may include IPA-3 and PF-3758309. Other agents may target PAK1 through off-target effects while targeting other PAK or unrelated proteins. The PAK1 inhibitor is administered in pharmacologically acceptable compositions using suitable routes of administration and dosages as described in more detail below and as can be recognized and appreciated by one of ordinary skill in the art.

g) Determining Resistance

Also provided herein are methods for determining resistance of a cancer to a PI3K inhibitor. These methods may be incorporated into the methods for treating cancer in a subject. The methods may be useful in assessing resistance to PI3K inhibition in a variety of cancers types as described. After a test has been performed on a sample, a result of the test is reported, for example, to the subject, the subject's physician, or a treatment institution treating the subject.

The methods may include measuring the level of PAK1 expression in a sample obtained from a subject. Our data indicated that PAK1 expression varies continuously and that a progressively higher level of PAK1 expression progressively indicates resistance to PI3K inhibition therapy. PAK1 expression above a control may indicate that the cancer is resistant to treatment with a PI3K inhibitor. For example, a level of PAK1 expression in a sample that exceeds PAK1 expression in matched sample of noncancerous tissue may indicate that the cancer is resistant to treatment with a PI3K inhibitor. In another example, a level of PAK1 expression in a sample that exceeds PAK1 expression in a PI3K-inhibition-resistant cell line of the same cancer type may indicate that the cancer is resistant to treatment with a PI3K inhibitor. In another example, a sample with a level of PAK1 expression that corresponds to a value of more than about 64, more than about 128, more than about 140, more than about 150, more than about 160, more than about 170, more than about 180, more than about 190, more than about 200, more than about 210, more than about 220, more than about 230, more than about 240, more than about 250, more than about 256, more than about 260, more than about 270, more than about 280, more than about 290, more than about 300, more than about 350, more than about 400, more than about 450, more than about 500, or more than about 512 arbitrary units (Affymetrix MASS normalized data) may indicate that the cancer is resistant to treatment with a PI3K inhibitor.

3. Pharmaceutical Compositions

The present disclosure also provides pharmaceutical compositions comprising a PI3K inhibitor and a PAK1 inhibitor. The disclosed pharmaceutical compositions include a PI3K inhibitor, a PAK1 inhibitor, and one or more pharmaceutically acceptable excipients. Various excipients may be suitable for use in the disclosed compositions, as will be recognized by one having ordinary skill in the art. One of ordinary skill in the art will also recognize a range of suitable concentrations for the excipients, the PI3K inhibitor, and the PAK1 inhibitor used in the disclosed compositions. The compositions may exhibit different formulations appropriate for different routes of administration, as would be understood and can be envisioned by one of ordinary skill in the art.

While compounds such as PI3K and PAK1 inhibitors may be administered alone in the various methods described herein, they may also be presented singly or together in one or more pharmaceutical compositions (e.g., formulations). In each composition the compounds may be formulated with one or more pharmaceutically acceptable carriers, adjuvants, excipients, diluents, fillers, buffers, stabilizers, preservatives, lubricants, or other materials well known to those skilled in the art and optionally other therapeutic or prophylactic agents.

Accordingly, the methods described herein include administration of one or more pharmaceutical compositions, as discussed herein, in which a compound such as PI3K or a PAK1 inhibitor is admixed together with one or more pharmaceutically acceptable carriers, excipients, buffers, adjuvants, stabilizers, or other materials, as described herein. Suitable carriers, excipients, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods known in the art of pharmacy. Such methods include the step of bringing into association the active compound(s) with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration (e.g. by injection, including cutaneous, subcutaneous, intramuscular, intravenous and intradermal), include aqueous and nonaqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate and nanoparticulate systems which are designed to target the active compound to blood components or one or more organs.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichlorotetrafluoroethane, carbon dioxide, or other suitable gases. Further formulations suitable for inhalation include those presented as a nebulizer.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

It will be appreciated that appropriate dosages of the PI3K inhibitor and/or PAK1 inhibitor, and compositions comprising a PI3K inhibitor and/or a PAK1 inhibitor, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

A suitable dosage range for the PI3K inhibitor and/or for the PAK1 inhibitor may be, for example, from about 0.01 to about 1000 mg per day, such as, for example, from about 0.1 to about 800 mg per day, from about 1 to about 500 mg per day, and from about 10 to about 200 mg per day.

The present invention can be utilized as illustrated by the following non-limiting examples.

Example 1

Materials Relating to Example 2

The examples provided in Examples 1 and 2 parallel methods and results reported in Zhang J, et al., Genetic heterogeneity of diffuse large B-cell lymphoma, *Proc. Acad. Sci. USA,* 110(4):1398-1403 (2013), the contents of which are hereby incorporated by reference.

Sample Acquisition and Processing.

Archival lymphoma tumors (N=73) and normal tissue (N=34) from 73 patients were obtained from the institutions that constitute the Hematologic Malignancies Research Consortium (HMRC). These cases were anonymized, shipped to Duke University, and processed in accordance with a protocol approved by the Institutional Review Board at Duke University. RNA and genomic DNA were extracted from these 73 cases in addition to 21 DLBCL cell lines using column-based methods, as described in Jima, D. D. et al., Deep sequencing of the small RNA transcriptome of normal and malignant human B cells identifies hundreds of novel microRNAs, *Blood* 116, e118-27 (2010), the contents of which are incorporated by reference.

Exome Sequencing.

Libraries were prepared as described in the Agilent SureSelect protocol, with modifications to adapter sequences and addition of a sample pooling step prior to exome capture in order to enable multiplexing. Specifically, sheared DNA was purified, resuspended in 10 mM Tris-Cl pH 8.5, quantified on the BioAnalyzer DNA1000 chip, end-repaired, and A-tailed. 5prime barcoded adapters were prepared by annealing complementary oligos as shown in Table 2.

TABLE 2

Sequences for barcoded 5 prime adapters.

| Pool | Strand 1 sequence, 5' to 3' | Strand 2 (Complement) sequence, 5' to 3' | Barcode sequence |
|---|---|---|---|
| 1 | ACACTCTTTCCCTACACGACGCTCTTCCGATCTGCCTAAT (SEQ ID NO: 1) | TTAGGCAGATCGGAAGAGCGTCGTGTAGGGAAAGAGT GT (SEQ ID NO: 2) | GCCTAA (SEQ ID NO: 3) |
| | ACACTCTTTCCCTACACGACGCTCTTCCGATCTGTAGCCT (SEQ ID NO: 4) | GGCTACAGATCGGAAGAGCGTCGTGTAGGGAAAGAGT GT (SEQ ID NO: 5) | GTAGCC (SEQ ID NO: 6) |

TABLE 2-continued

Sequences for barcoded 5 prime adapters.

| Pool | Strand 1 sequence, 5' to 3' | Strand 2 (Complement) sequence, 5' to 3' | Barcode sequence |
|------|------------------------------|-------------------------------------------|------------------|
| 2 | ACACTCTTTCCCTACACGACGCTCTTCCGATCTTGG TCAT (SEQ ID NO: 7) | TGACCAAGATCGGAAGAGCGTCGTGTAGGGAAAGAGT GT (SEQ ID NO: 8) | TGGTCA (SEQ ID NO: 9) |
|   | ACACTCTTTCCCTACACGACGCTCTTCCGATCTATT GGCT (SEQ ID NO: 10) | GCCAATAGATCGGAAGAGCGTCGTGTAGGGAAAGAGT GT (SEQ ID NO: 11) | ATTGGC (SEQ ID NO: 12) |
| 3 | ACACTCTTTCCCTACACGACGCTCTTCCGATCTGAT CTGT (SEQ ID NO: 13) | CAGATCAGATCGGAAGAGCGTCGTGTAGGGAAAGAGT GT (SEQ ID NO: 14) | GATCTG (SEQ ID NO: 15) |
|   | ACACTCTTTCCCTACACGACGCTCTTCCGATCTTCA AGTT (SEQ ID NO: 16) | ACTTGAAGATCGGAAGAGCGTCGTGTAGGGAAAGAGT GT (SEQ ID NO: 17) | TCAAGT (SEQ ID NO: 18) |
| 4 | ACACTCTTTCCCTACACGACGCTCTTCCGATCTCTG ATCT (SEQ ID NO: 19) | GATCAGAGATCGGAAGAGCGTCGTGTAGGGAAAGAGT GT (SEQ ID NO: 20) | CTGATC (SEQ ID NO: 21) |
|   | ACACTCTTTCCCTACACGACGCTCTTCCGATCTAAG CTAT (SEQ ID NO :22) | TAGCTTAGATCGGAAGAGCGTCGTGTAGGGAAAGAGT GT (SEQ ID NO: 23) | AAGCTA (SEQ ID NO: 24) |

After annealing, 5p adapters were mixed in equimolar ratio with universal 3p adapters (which have sequences identical to the Illumina PE sequence) and diluted to the same concentration as Illumina adapters. 8 barcoded adapters were mixed in pairs as indicated in the adapter sequence table, so that two barcoded adapters could be ligated to each sample. The purpose of assigning two barcodes per sample was to reduce possible barcode-specific bias and increase sequence diversity in the beginning of the reads, when clusters are resolved. The adapter:DNA ligation ratio was 2 μl adapter pool per μg of sheared DNA, as determined by BioAnalyzer. The ligated library was amplified by Illumina PE PCR primers and 2× Phusion HF Master Mix. Post-PCR, the library was purified and assayed on BioAnalyzer to determine size and concentration.

Four libraries (125 ng each) were pooled, vacuum-dried at 45° C., and resuspended in 3.4 μl water. Libraries were blocked and prepared according to Agilent protocol and hybridized against Agilent SureSelect All Exome baits for 24 hours at 65° C. in a thermal cycler. The biotinylated exome baits, with exonic DNA hybridized, were purified on SPRI magnetic beads (Agilent) and washed three times according to Agilent SureSelect protocol. The capture library pool was amplified with 12 cycles of PCR, and molarity and size distribution were measured by BioAnalyzer. Libraries were diluted to 5 pM for Illumina clustering and paired-end sequenced over 9 days.

Identification of DLBCL Cancer Genes.

Genes mutated in DLBCL were identified by analyzing the 73 primary tumor samples. The initial set of DLBCL mutations were determined from the 34 DLBCL primary tumors with paired normal samples, which constituted the discovery set. Data from cell lines were not used in this analysis. For each of these cases, mutations were identified that were present in tumor but absent from the paired normal cases (somatically mutated). A total of 426 genes that were recurrently mutated. Excluding those for which more than two-thirds of the variants also were found by the NHLBI Exome Sequencing Project, 322 genes remained, including PIK3CD, PIK3R1, and MTOR. Those 322 genes (Dataset S3) comprised 1418 variants, including three for PIK3CD, three for PIK3R1, and five for MTOR.

Cell Culture.

FL5.12 myristoylated Akt (myrAkt) cells obtained from Jeffrey Rathmell's laboratory were cultured in RPMI (Invitrogen, 11875-093) supplemented with 10% FCS, 500 pg/mL recombinant mouse IL3 (rmIL3), 2 mM L-glutamine, 10 mM HEPES, 1% v/v Penicillin/Streptomycin (Invitrogen, 15140-122) and 0.1% v/v βME (Invitrogen, 21985-023). Cells were split down to a density of 50 k/ml daily.

Lymphoma cell lines were cultured with RPMI1640 media supplemented with 10% v/v Fetal Bovine Serum (FBS) and 1% v/v Penicillin/Streptomycin supplied at 10,000 U penicillin and 10 mg streptomycin/ml (BJAB, Farage, Karpas422, Pfieffer, RL, SCI 1, SKI, Toledo, U2932, WSU_NHL, HT), or RPMI1640 supplemented with 15% v/v FBS and 1% v/v P/S (RCK8, SUDH4, SUDHL7), Iscove's modified Dulbecco's medium (IMDM) supplemented with 20% v/v human plasma and 1% P/S (RCK8, SUDHL4, SUDHL7), or alpha-MEM media supplemented with 10% FBS and 1% P/S (TMD8). Cells were grown in a 5% CO2 environment at 37° C.

PIK3CD Wild-Type and Mutant Expression Constructs.

The PIK3CD shuttle clone (Genecopoeia, GC-M0163-CF) open reading frame was inserted into the pEF-DEST51 plasmid (Invitrogen, 12285-011) using Gateway cloning (Invitrogen, 12538-120). The point mutation was created by site-directed mutagenesis (Stratagene, 200521). Wild-type and mutant PIK3CD plasmid insert sequences were confirmed over the entire length of the ORF by Sanger sequencing.

Transfection of FL5.12 mAkt Cell Lines, IL3 Withdrawal.

For western blot analysis, 1.5 million FL5.12 myrAkt cells were transfected with 2 μg wild-type or mutant by Amaxa (Nucleofector V, program G-016), concurrent with addition of doxycycline at 1 μg/ml in the media to induce myrAkt expression. At 18 hours post-transfection, each transfection was split in half and washed twice in Phosphate-buffered saline. The control cells were re-suspended in normal FL5.12 growth media, whereas the remainder was re-suspended in media lacking IL3. P-Akt was measured by Western blots 3 hours later to compare the cells in which IL3 was replaced to those in which it was withdrawn. Cells for PI3K activity ELISA were transfected in a similar manner, but with 50 M cells transfected in 5 batches of 10M cells by Amaxa. Cells were also subject to IL3 withdrawal 18H post-transfection and harvested 3 hours later.

Western Blot.

RIPA lysis buffer (1× phosphate-buffered saline [PBS], 1% Nonidet P-40, 0.5% sodium deoxycholate, 0.1% SDS, 10 mM phenylmethylsulfonyl fluoride, 1 µg/mL aprotinin, and 100 mM sodium orthovanadate) was added to 750,000 cells and incubated on ice for 30 minutes. The mixture was spun down and the supernatant was transferred to a new tube as the whole cell extract. A total of 20 µg of cell lysate was separated on a 4-18% Tris-Bis NuPAGE gel (Invitrogen) and transferred using the iBlot transfer device (Invitrogen) program 2 for 6 minutes. The blots were probed using 1:1000 rabbit-phospho-AKT (Cell Signaling Technologies, #4060), 1:2000 rabbit totalAKT (Cell Signaling Technologies, #9272) and 1:1000 mouse-anti-β-actin (Santa Cruz Biotechnologies, sc-47778) overnight at 4° C. The antibodies were detected using 1:10,000 goat-anti-rabbit or 1:10,000 goat-anti-mouse horse radish peroxidase conjugated antibodies (Santa Cruz Biotechnologies). Western Blotting Luminol Reagent (Santa Cruz Biotechnologies) was used to visualize the bands corresponding to each antibody.

Cell Viability Assays.

The effect the PI3K inhibitor drug BKM120 (Novartis) on lymphoma cell lines was assayed on 96-well format using MTT viability assays. 40,000 cells were grown in drug at 10 concentrations: 25 µM, and nine serial 1:2 dilutions down to 0.05 µM. For each condition tested, there were five technical replicates. Two controls were included: media only and drug-free cells. If the IC50 was not reached within this drug concentration range, the experiment was repeated with an additional drug concentration of 5004. After 48 hours, 15 µl MTT was added to each well, and the plate was incubated at 37° C. for 4 hours. 100 µl of MTT detergent solution was added, and color was developed in the dark at room temperature overnight, after which 570 nm absorbance was measured. After normalization to control wells, the IC50 values were calculated. An IC50 value represents the drug concentration needed to achieve 50% growth inhibition.

Example 2

Identification of PIK3CD as an Oncogene

The results of Example 2 are shown in FIG. 1. Mutations to the PIK3CD gene were observed in three separate DLBCL tumors; evidence of one such mutation (a transversion from T to G) is shown on paired deep sequencing reads (FIG. 1A) and Sanger sequencing chromatograms (FIG. 1B) for normal tissue and tumor tissue from the same case. The sequenced bases differ in only a single nucleotide that appears as a G in the tumor and a T in the matched normal sample. That mutation altered an encoded amino acid in the catalytic domain of the PIK3CD gene from an uncharged asparagine residue to one with a positively charged side chain (lysine). Mutations were detected in two additional genes in the PI3K pathway—PIK3R1 and MTOR—pointing to deregulation of the PI3K pathway as an important oncogenic mechanism in DLBCLs. The observed mutations spread across multiple locations in those genes (FIG. 1C). FIG. 1D shows a structural model of the predicted protein structure expressed from the PIK3CD gene.

Wild-type and mutant PIK3CD constructs were overexpressed in FL5.12 lymphoma cells, which exhibits IL3-dependent PI3K signaling. In normal FL5.12 cells, the withdrawal of IL3 is associated with a measurable decrease in PI3K signaling and decreased phosphorylated Akt. In FL5.12 cells overexpressing the wild-type form of PIK3CD, withdrawal of IL3 was associated with a measurable decrease in phosphorylated Akt, while no measurable decrease was observed in cells overexpressing the mutant form of PIK3CD (FIGS. 1E, 1F). The results indicate that the observed mutation in the PIK3CD gene had an activating effect on PI3K function.

In addition, testing for MTOR mutations was performed on 21 established DLBCL cell lines (BJAB, Farage, Karpass422, Ly10, Ly19, Ly3, Ly7, Ly8, Pfieffer, RCK8, RL, SCI 1, SKI, SUDJL4, TDM8, Toledo, U2932, WSU_NHL, HT, Ly1, and SUDHL7). Three of those cell lines (HT, Ly1, and SUDHL7) were shown to contain MTOR mutations, and those three cell lines had, on average, a fivefold higher sensitivity to the PI3K inhibitor BKM120 than the other 18 cell lines lacking such mutations (FIG. 1G).

Example 3

Materials Relating to Examples 4-7

The examples provided in Examples 3-7 parallel methods and results reported in Walsh K., et al., PAK1 Mediates Resistance to PI3K Inhibition in Lymphomas, *Clin. Cancer Res.*, 19(5):1106-15 (2013), the contents of which are hereby incorporated by reference.

Cell Culture.

A total of 60 cell lines representative of different cancer types were obtained from the ATCC and grown and maintained in accordance with the provided guidelines. The cell lines represented the following distinct histologies: mantle cell lymphoma (5 lines: JVM13, Rec1, Mino, JVM2, Jeko); germinal center B-cell derived ("GCB") DLBCL (19 lines: Farage, BJAB, Ly1, Ly2, Ly7, Ly8, Ly19, HBL2, HT, Karpas422, Pfeiffer, RCK8, RL, Sci-1, Ski, SUDHL4, SUDHL7, Toledo, WSU-NHL); primary mediastinal B-cell lymphoma ("PMBL") (3 lines: K1106, MEDB1, U2940); Burkitt lymphoma (11 lines: Daudi, CA46, EB1, EB2, EB3, Jijoye, Raji, Ramos, Namwala, BL2, BL41); Hodgkin lymphoma (3 lines: RMPI6666, L1236, L428); activated B-cell derived ("ABC") DLBCL (6 lines: Ly3, HBL1, TMD8, Ly10, Riva, U2932); multiple myeloma (6 lines: U266, SKMM1, RPMI8226, KMS12, IM9, H929); acute myelogenous leukemia ("AML") (2 lines: U937, KG1); acute lymphoblastic leukemia ("ALL") (2 lines: Reh, SR); and T-cell lymphoma (3 lines: Molt4, RPMI8402, Jurkat). The cell lines were tested within six months after resuscitation.

Small Molecule Inhibitors.

The PI3K p110 inhibitor BKM120, the dual PI3K/mTOR inhibitor BEZ235, and the dual PI3K/mTOR inhibitor BGT226 were obtained from Novartis. The PAK1 inhibitor IPA-3 was purchased from Tocris Bioscience.

Cell Viability.

The 3-(4,5-dimethylthiazol-2-yl)-2,5-diphenyltetrazolium bromide (MTT) cell viability assay was used to determine cell viability in response to drug treatment. Five replicates per concentration tested were carried out in serial dilutions with a total of ten concentrations with a 50% reduction in drug concentration per dilution for each plate. A total of 15 µl of MTT reagent was added to each drug-treated well and incubated for three hours in 37° C. Detergent was added to each drug-treated well and incubated overnight at room temperature without exposure to light. Absorbance was measured at 570 nm using a plate reader from Tecan Group. The IC50 concentration was determined using the publicly available ED50 plus v1.0 software program.

Western Blot.

RIPA lysis buffer (1×PBS, 1% NP-40, 0.5% sodium deoxycholate, 0.1% SDS, 10 mmol/L sodium orthovanadate) was added to 750,000 cells and incubate on ice for 30 minutes. The mixture was spun down, and the supernatant was transferred to a new tube as the whole-cell extract. A total of 20 µg cell lysate was separated on a 4% to 18% Tris-Bis NuPAGE gel (Invitrogen) and transferred using the iBlot transfer device (Invitrogen) program 3 for seven minutes. The blots were probed with a 1:100 p-AKT, 1:1000 total AKT, 1:100p-GSK3alpha, 1:100 p-GSK3beta, or 1:100 p-s6 (Cell Signaling), or 1:5000 goat anti-β-actin (SC-47778, Santa Cruz Biotech) for one hour at room temperature. The antibodies were detected by the use of 1:10,000 goat anti-mouse-HRP conjugated antibodies (Santa Cruz Biotech). Western Blotting Luminol Reagent (Santa Cruz Biotech) was used to visualize the bands corresponding to each antibody.

Confirmation of Pathway Downregulation.

One million BJAB DLBCL cells were treated with increasing doses of BEZ235, and, after six hours, the cells were analyzed for a dose-dependent effect at 15, 30, 60, 125, 250, and 500 nmol/L concentrations. Cell count and viability were measured for each concentration. To perform a time course analysis, BJAB cells were treated with BEZ235 at 30 nmol/L (selected on the basis of its IC50 concentration of 0.0269 mmol/L), and cell count was measured at zero, three, and six hours after treatment. Western blot analyses were performed to assess phosphorylation of AKT, GSK3alpha, GSK3beta, and S6.

Gene Expression Profiling and Statistical Analysis.

Gene expression profiling using Affymetrix Gene 1.0 ST arrays were carried out, scanned, and normalized as described in Jima, D. D. et al., Deep sequencing of the small RNA transcriptome of normal and malignant human B cells identifies hundreds of novel microRNAs, *Blood* 116, e118-27 (2010). Gene expression data for 60 cell lines were divided into training (n=29) and validation (n=31) sets. In the training set, the Cox proportional hazards regression model was applied to identify genes associated with a response to BEZ235. BEZ235 was the first drug tested in all of the cell lines. The associations between BEZ235 and gene expression served as the starting point for the exploration of the molecular predictors of response. In all cases, the experimentally identified IC50 for each of three drugs for the cell lines were considered the response variable.

To identify overlap between genes associated with a response to each of the three drugs, the Cox model was applied to the entire drug-response data for all the available cell lines. Genes associated with a response to BEZ235 (n=60) and BKM120 (n=60) were deemed significant at P less than 0.01 and those associated with a response to BGT226 (n=31) were deemed significant at P less than 0.05. Two-tailed probabilities were used in all analyses involving BEZ235 and 1-tailed probabilities were used with BKM120 and BGT226, with the direction of the effect being indicated by the association with response to BEZ235 in the same cell lines.

The Cox model identified genes that were associated with a response to BEZ235. In sum, 881 genes were identified as being associated with a response to the drug (P<0.05) in the training set of 29 cell lines. Hierarchical clustering was applied to those genes identified in the training set, creating two predominant clusters of cases in the training set. Those clusters served as the base model for identifying additional cell lines that were sensitive or resistant to BEZ235. Those clusters were then used to construct a Bayesian model to predict the sensitivity or resistance to the independent validation set cases treated with BGT226 and BKM120. A posterior probability value of 0.9 or higher was used to signify predicted sensitive cell lines and posterior probability value of 0.1 or lower was used to signify predicted resistant cell lines. The Wilcoxon-rank test was used to identify differences between IC50s of the predicted sensitive and resistant groups.

RNA Interference.

Lentiviral pGIPZ constructs containing either a scrambled sequence (non-silencing; cat. no. RHS4346; Open Biosystems) as control, or a hairpin sequence targeting the PAK1 gene (cat. no. RHS4430; Open Biosystems) were mixed with Lentiviral packaging mix (cat. no. TLP4691; Open Biosystems) and transfected into TLA-HEK-293T cells using Arrest-in as a transfection reagent. Virus was harvested 72 hours post-transfection and frozen at −80° C. until use. DLBCL cell lines were infected with virus in the presence of 8 µg/µl of polybrene, using $1 \times 10^5$ cells per well in a 6-well plate. The plates containing cells and virus were spun at 700 g for 90 minutes at room temperature. Cells were selected by puromycin at 72 hours post-infection and observed to express GFP. Successful knockdown of PAK1 was confirmed by Western blot and quantitative PCR. The DLBCL line Ly8 was selected for its transfectability, relatively high PAK1 expression, and relatively high (resistant) IC50 for BEZ235.

Synergy Testing Between Small-Molecule Inhibitors.

BEZ235 was tested in combination with the PAK1 inhibitor IPA-3 using Calcusyn software by applying the Chou-Talalay method. BJAB, HBL1, HBL2, HT, Ly8, and Riva cells were tested, as were normal tonsil lymphocytes. Ly8 and tonsillar lymphocytes were cultured in 96-well plates (approximately 500,000 cells/ml) for 36 hours in Iscove's modified Dulbecco's medium (IMDM) with 20% human AB serum. Viability was assessed with alamar blue dye and normalized to the lowest concentration of BEZ235 in each group.

Example 4

PI3K Inhibition in Cancer Cell Lines

Figure 2:
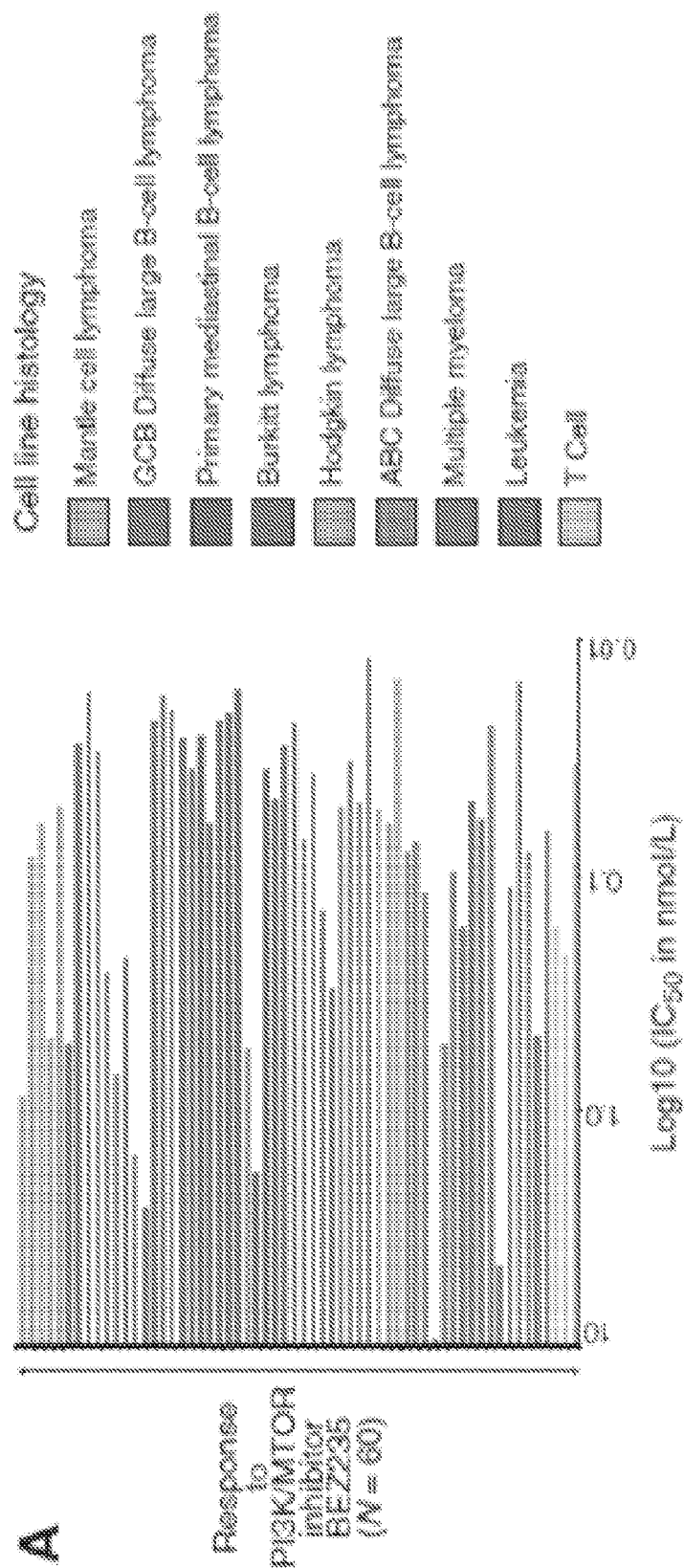
FIG. 2 shows that PI3K inhibition is effective in a broad range of blood cancer histologies, with as much as 10-fold variation in sensitivity to PI3K inhibitors observed between individual cell lines within the various histologies.
Figure 2:
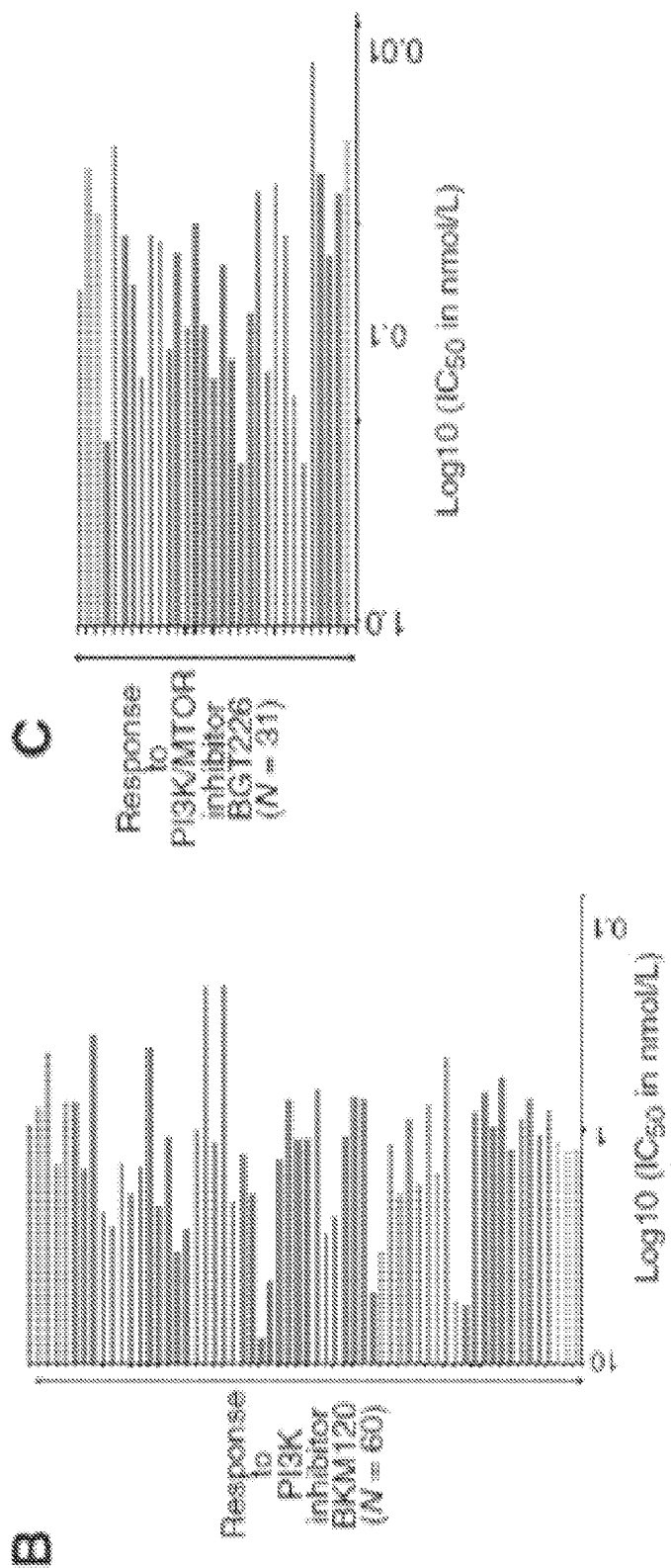
Figure 2:
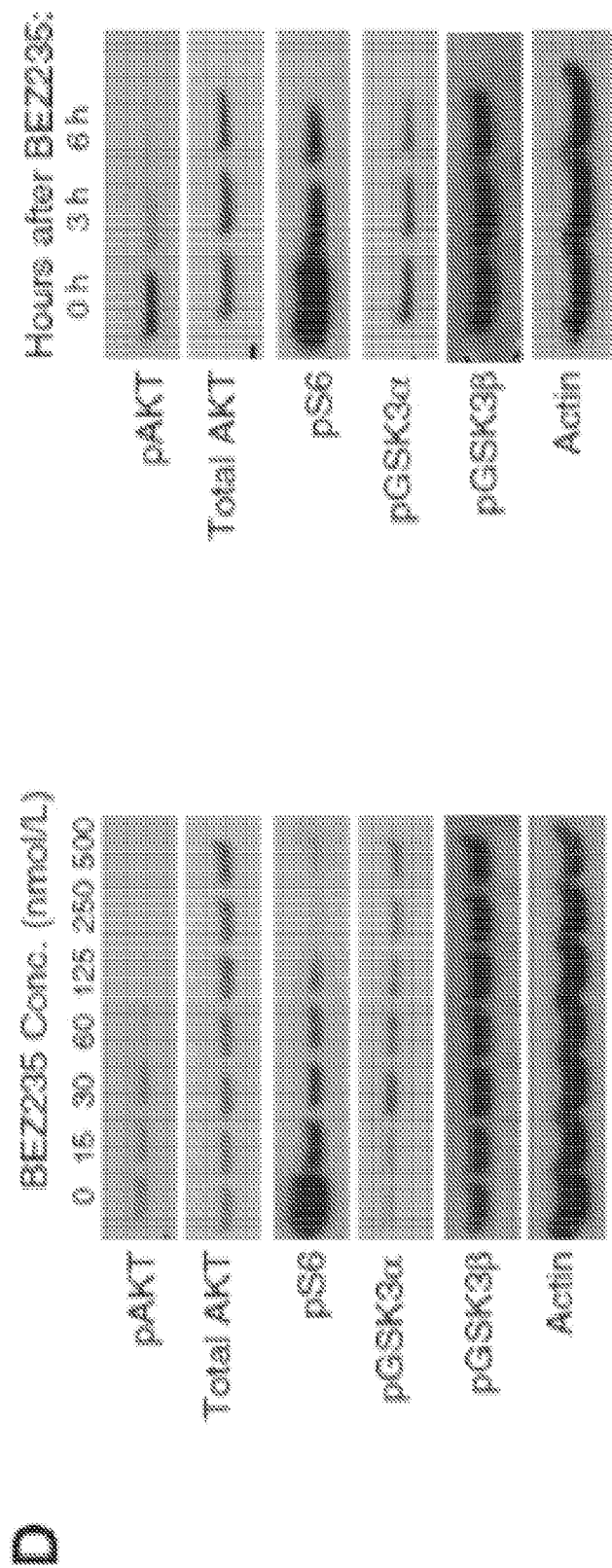

Sixty cell lines representing mantle cell lymphoma, germinal center B-cell derived DLBCL, primary mediastinal B-cell lymphoma, Burkitt lymphoma, Hodgkin lymphoma, activated B-cell derived DLBCL, multiple myeloma, acute myelogenous leukemia, acute lymphoblastic leukemia, and T-cell lymphoma were tested for sensitivity to PI3K inhibition by BKM120, BEZ235, and BGT226. BKM120 and BEZ235 were tested in all 60 cell lines; BGT226 was tested in 31 cell lines. The observed IC50s ranged from 0.01 to 9 µmol/L for BEZ235, 0.003 to 0.2 µmol/L for BGT226, and 0.2 to 7.8 µmol/L for BKM120. FIGS. 2A-C show the drug response to each drug for each cell line in logarithmic scale. All three drugs were nearly 100% lethal at 48 hours. The results show that the three tested PI3K inhibitors were effective at physiologically achievable concentrations and that PI3K inhibition is broadly effective as a therapeutic strategy against cancers such as blood cancers. Within nearly every histology tested, the respective cell lines varied by as much as 10-fold in their sensitivity to the drugs tested. Generally, the histology of a cell line was not associated with response to a drug; the observed heterogeneity in drug response within a particular histology was generally comparable with that observed between different histologies.

Pair-wise cross-histology comparisons between all histology groups were conducted using the Wilcoxon-rank test, adjusted for multiple comparisons using the Bonferroni method, to examine the role of histology in the response to PI3K inhibitors. The association between histology and response to the inhibitors was similar to that expected by chance alone (adjusted P>0.05 in all cases).

Inhibition of the PI3K pathway by the three PI3K inhibitors was confirmed through separate time-course and dose-escalation experiments, as well as by measuring the expression of key downstream members of the pathway. The drugs were tested in the BJAB DLBCL for their effects on p-AKT, p-S6, p-GSKalpha, and p-GSKbeta. FIG. 2D shows exemplary Western blots resulting from those experiments. As shown in the left panel of FIG. 2D, a dose-dependent down regulation of the various PI3K targets was observed at six hours after drug treatment, while total AKT and actin controls remained unchanged. In addition, the right panel of FIG. 2D demonstrates a time-dependent down regulation of the same PI3K targets at three and six hours after treatment with 30 nmol/L BEZ235 (near the observed IC50 of 26.9 nmol/L) with no corresponding change to total AKT and actin controls. An associated decrease in cell viability was ruled out by quantifying the proportion of viable cells at each time point using trypan blue staining. The results demonstrate that BKM120, BEZ235, and BGT226 directly inhibit the PI3K pathway.

Example 5

Gene Expression Profiles Associated with a Response to PI3K/mTOR Inhibition

Given the lack of correlation between histology and response to PI3K inhibition, the potential for an association across the histologies between gene expression profiles and response to PI3K inhibition was investigated.

Gene expression profiling was performed on all 60 cell lines. The cell lines were divided into a training set (n=29) and a validation set (n=31). All of the cell lines tested with BGT226 (n=31) were assigned to the validation set. The Cox proportional hazards model was applied to identify genes associated with IC50 (i.e., the response variable). The experiments identified 881 genes associated with a response to BEZ235 in the training set (P<0.05), which were associated with either relative sensitivity (i.e., lower IC50) or resistance (i.e., higher IC50).

Figure 3:
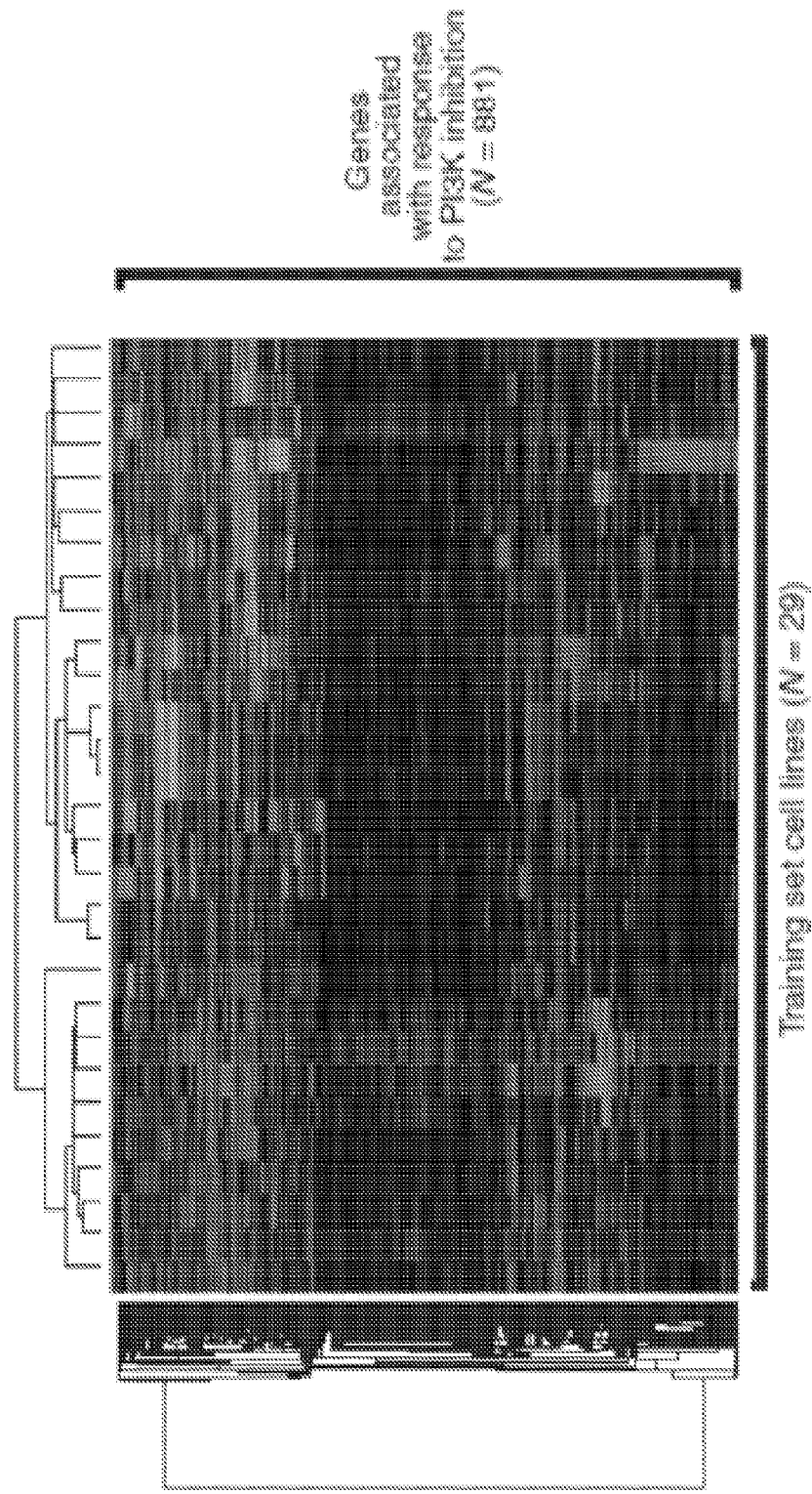
FIG. 3 shows that gene expression profiles correlate with sensitivity or resistance to PI3K inhibition across different blood cancer histologies.
Figure 3:
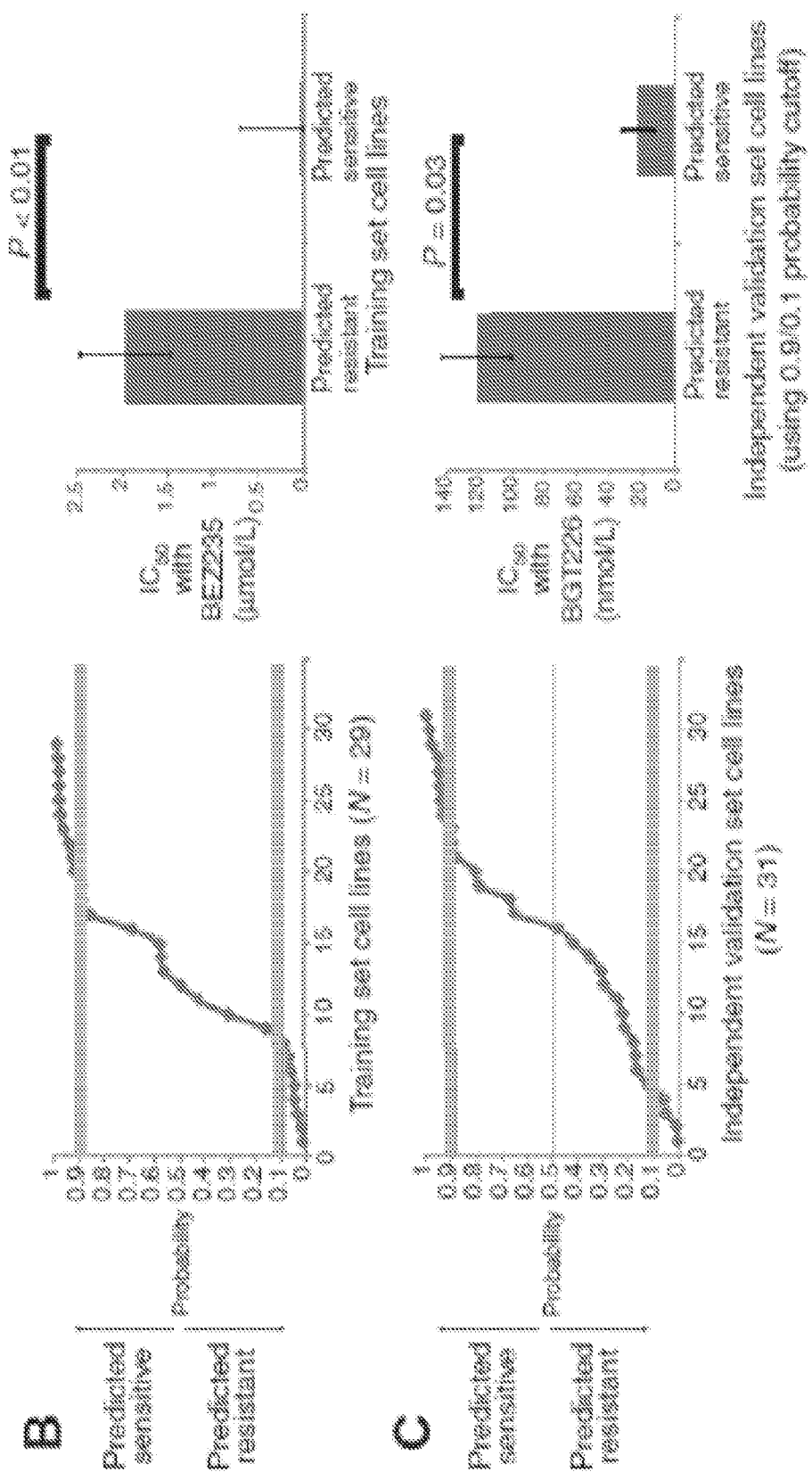
Figure 3:
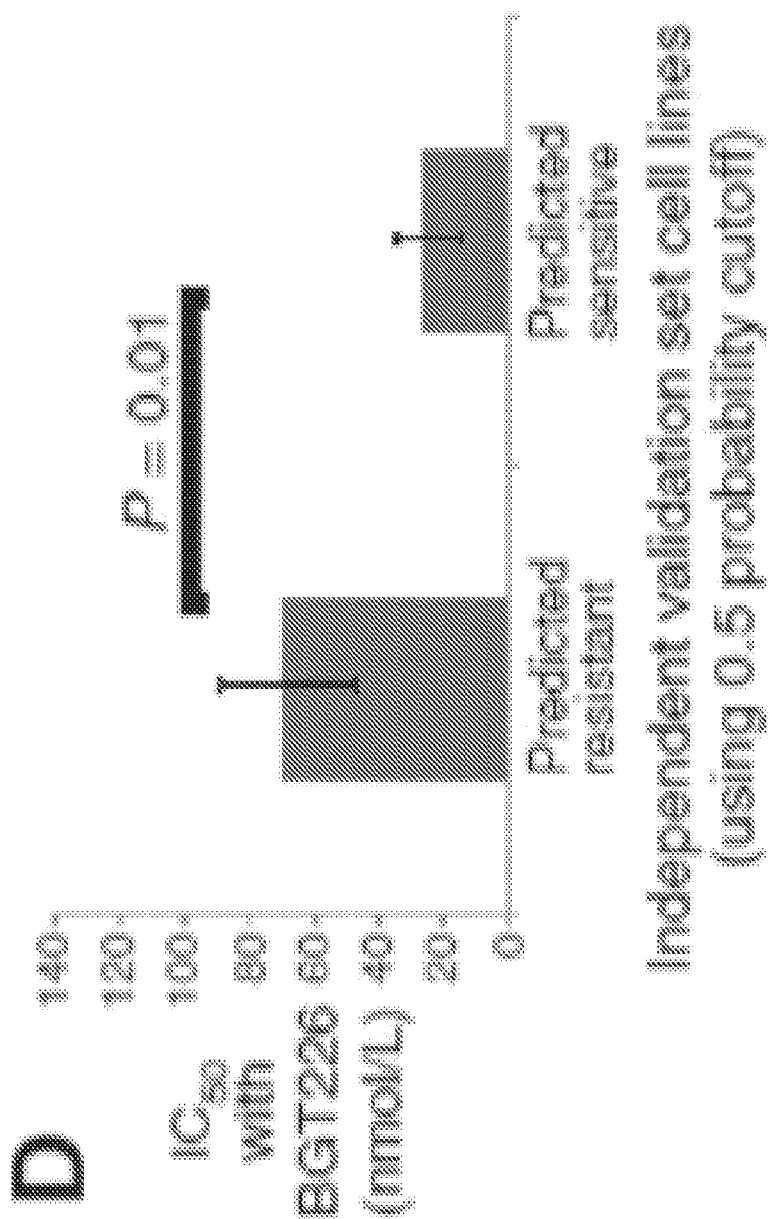

Hierarchical clustering on those 881 genes for all of the cases in the training set were used to group the cell lines on the basis of shared patterns of gene expression. FIG. 3A shows hierarchical clustering for the 881 genes associated with a response to BEZ235 in the training set cell lines, with a heat map representing the relative expression of those differentially expressed genes over a two-fold range (red, higher expression; green, lower expression). The cell lines segregated into two main clusters that were predicted to be either sensitive or resistant to BEZ235. Those data were used to generate a Bayesian predictor to identify cases in the training and validation sets that most closely resembled the observed clusters. For each case, the Bayesian model generated a probability that estimated the similarity of those cases with the original clusters.

In the training set, those cases with a Bayesian probability of 0.9 or higher were deemed as predicted sensitive to PI3K inhibition, and those with a Bayesian probability of 0.1 or lower were deemed as predicted to be resistant (FIG. 3B, left panel). The right panel of FIG. 3B shows that the training set cell lines treated with BEZ235 that were predicted to be either sensitive or resistant to PI3K inhibition differed more than 2-fold in their observed IC50s (P<0.01). As shown in FIG. 3C, similar results were observed in the validation set cell lines treated with BGT226. In addition, a similar trend emerged in the validation set cell lines treated with BEZ235, with a greater than 2-fold difference between the IC50s of the predicted sensitive and predicted resistant groups (P=0.14). Upon altering the Bayesian probability for identifying the predicted sensitive and resistant cases to greater or less than 0.5, respectively, the differences between the two groups remained significant (P=0.01), with a more than 2-fold difference of IC50s in the validation set cases treated with BGT226 (FIG. 3D). The genes associated with a response to the dual PI3K/mTOR inhibitors were not significantly associated with a response to the selective PI3K inhibitor, suggesting that the additional inhibition of mTOR might affect different mechanisms in the subject cell lines.

The potential role of PTEN mutations in the response to PI3K inhibition was evaluated in 21 DLBCL cell lines, with no PTEN mutations detected in those cell lines. Those results suggest that PTEN mutations are not a significant mediator of resistance to PI3K inhibition in the subject cells.

Taken together, the results suggest that the association of gene expression and drug response produced robust results for the dual PI3K/mTOR inhibitors.

Example 6

PAK1 Expression is Associated with Resistance to PI3K Inhibition

Figure 4:
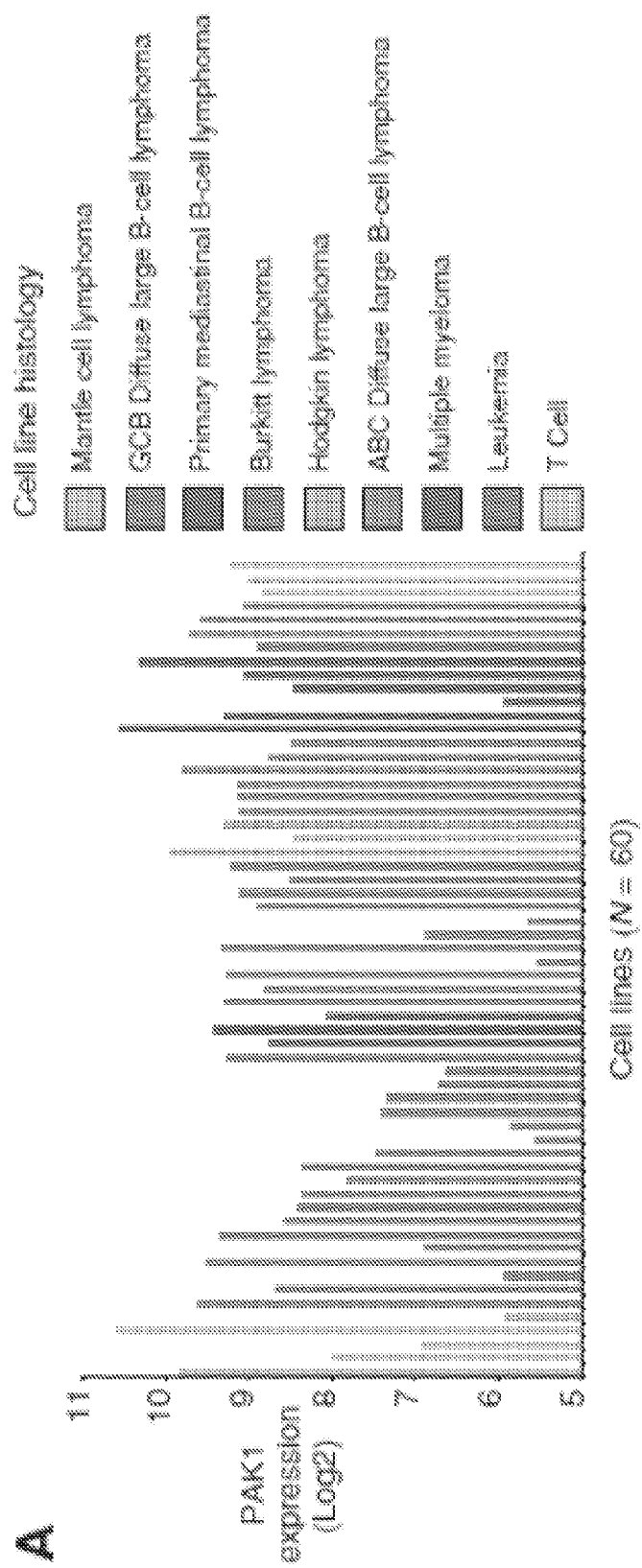
FIG. 4 illustrates that PAK1 expression varies among individual cell lines of different blood cancer histologies (FIG. 4A) and shows that the level of PAK1 expression correlates with sensitivity or resistance to PI3K inhibition (FIG. 4B). In addition, FIG. 4C demonstrates substantial variations among PAK1 gene and protein expression in primary human DLBCL samples.
Figure 4:
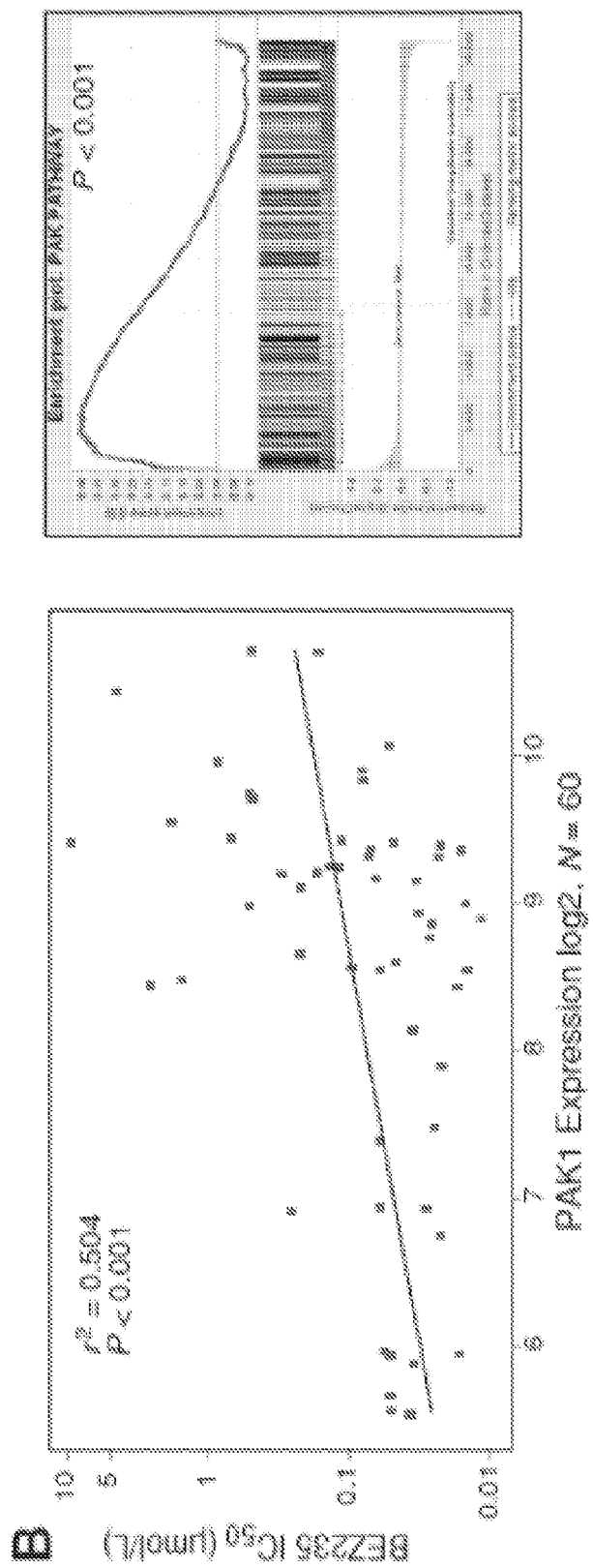
Figure 4:
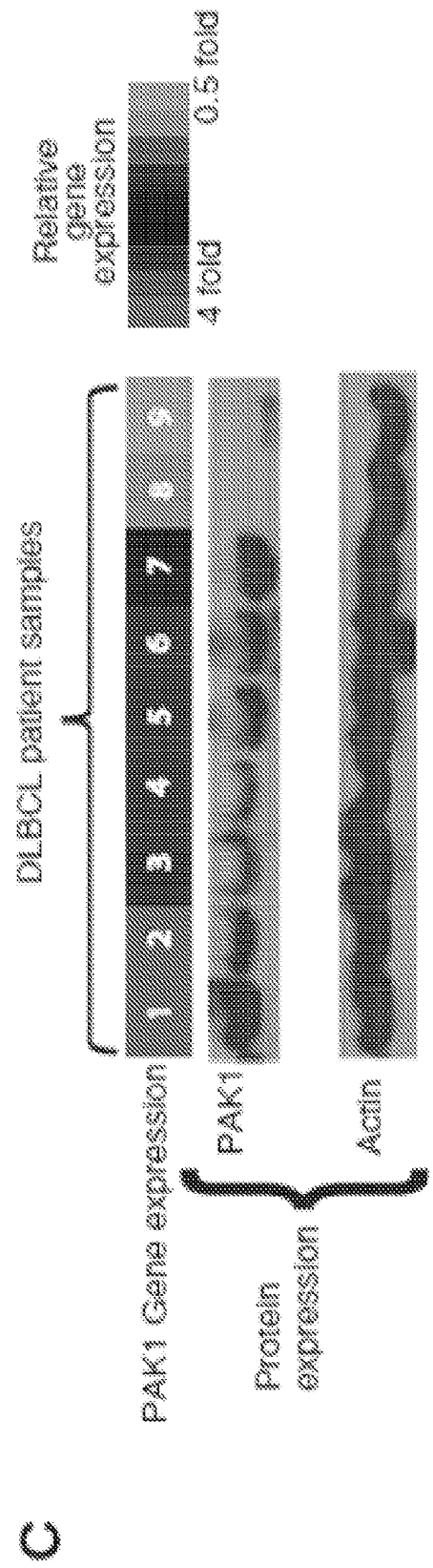

The inventors identified all genes that were associated with resistance to all three drugs: BEZ235 (n=60, P<0.01); BKM120 (n=60, P<0.01); and BGT226 (n=31, P<0.05). PAK1 was one of only two genes to meet those stringent criteria. As shown in FIG. 4A, PAK1 was robustly expressed in the 60 subject cell lines, but higher or lower expression of PAK1 was not histology-specific.

The left panel of FIG. 4B depicts the association between PAK1 expression and BEZ235 IC50 as a fitted linear regression ($r^2$=0.504, P=0.0005). Similar associations were observed between the expression of PAK1 and response to BKM120 (P=0.009) and the expression of PAK1 and response to BGT226 (P=0.03). In each case, higher PAK1 expression correlated with higher IC50s, i.e., resistance to PI3K inhibition. A gene enrichment analysis was performed to discern whether genes that were previously described as having a role in PAK signaling were differentially expressed among the cell lines identified as being sensitive or resistant to PI3K inhibition with BEZ235. The right panel of FIG. 4B shows the results of that analysis, indicating strong statistical evidence that the PAK pathway was significantly upregulated in the predicted resistant group of cell lines. In other words, the genes related to PAK signaling were expressed more highly in cell lines that were resistant to PI3K inhibition. The core group of enriched genes is depicted from the output of the program, and the overlap of higher expression and the genes in the pathway was noted to be highly significant (P<0.001).

In addition to cell lines, nine primary human samples were examined for PAK1 expression. In FIG. 4C, the top row shows PAK1 mRNA expression with red representing relatively high expression and green representing relatively low expression. The lower two rows of FIG. 4C show Western blot results indicating PAK1 protein expression (middle row) and actin expression (lower row) for the same samples. The results showed PAK1 mRNA and protein expression generally agreed well and that PAK1 was well expressed in a number of primary human DLBCL cases.

Taken together, the results suggest that PAK1 exerts important downstream effects that mediate resistance to PI3K inhibition.

Example 7

PAK1 Mediates Resistance to PI3K Inhibition

Two complementary approaches were used to inhibit PAK1 and examine the resulting effects on sensitivity to PI3K inhibition: RNA interference and small-molecule inhibition.

Figure 5:
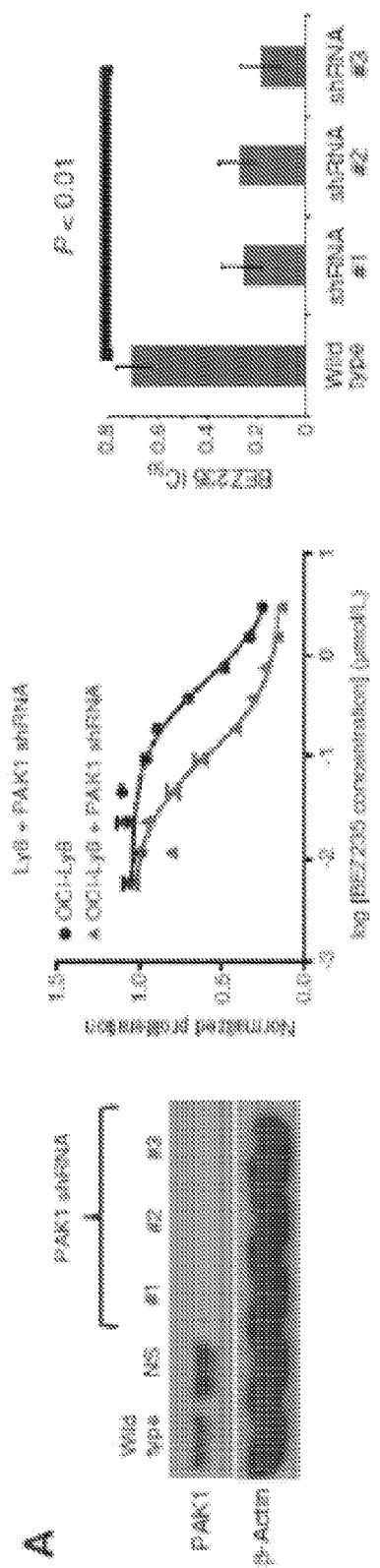
FIG. 5 demonstrates that resistance to PI3K inhibition can be overcome by inhibiting PAK1. Reduction of PAK1 expression in PI3K inhibitor-resistant DLBCL cells resulted in significantly increased sensitivity to a small-molecule PI3K inhibitor (FIG. 5A). In addition, the combination of a small-molecule PI3K inhibitor with a small-molecule PAK1 inhibitor was more effective than either drug alone (FIG. 5B), and the combination of PI3K and PAK1 inhibitors exhibited significant synergy in cells resistant to PI3K inhibition (FIG. 5C).
Figure 5:
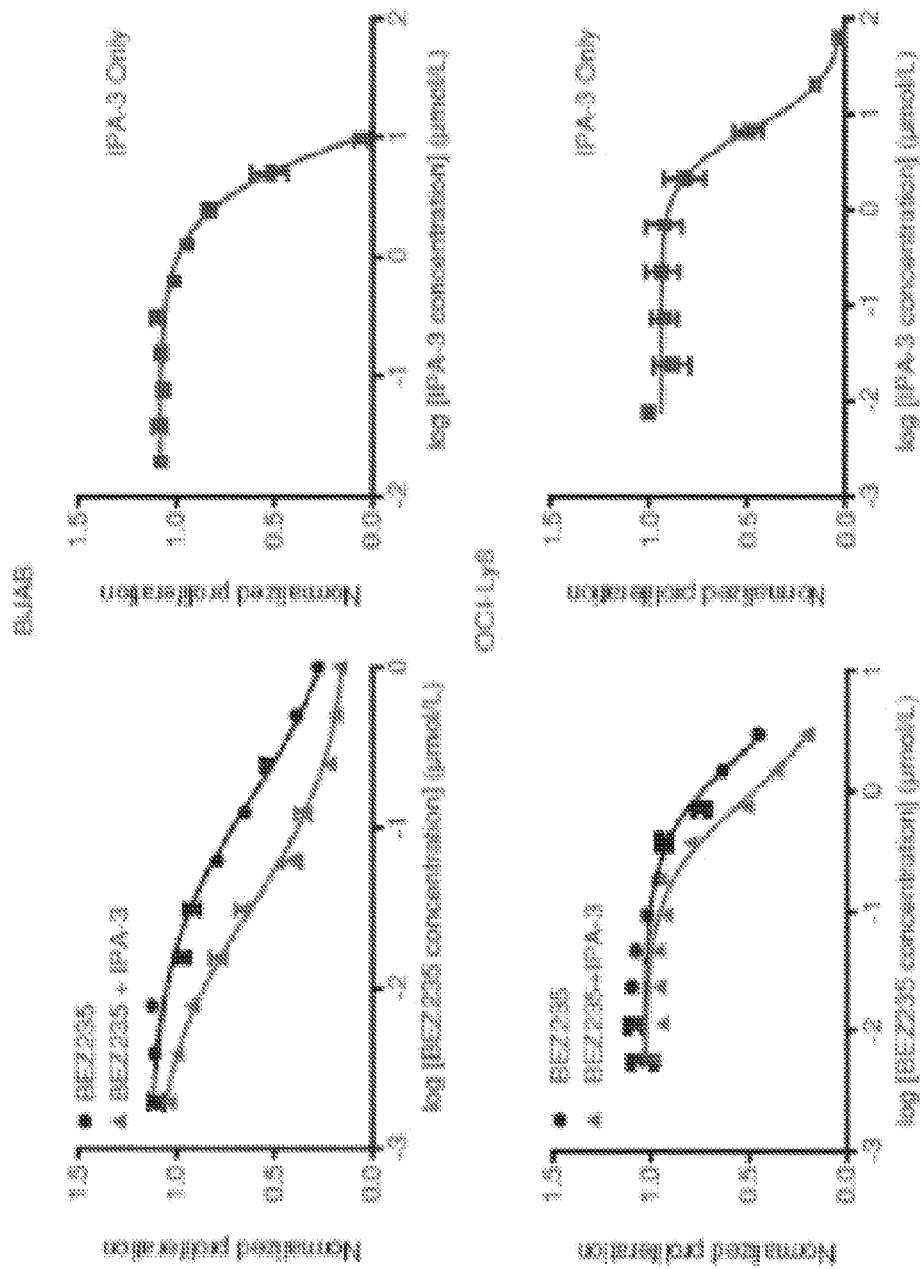
Figure 5:
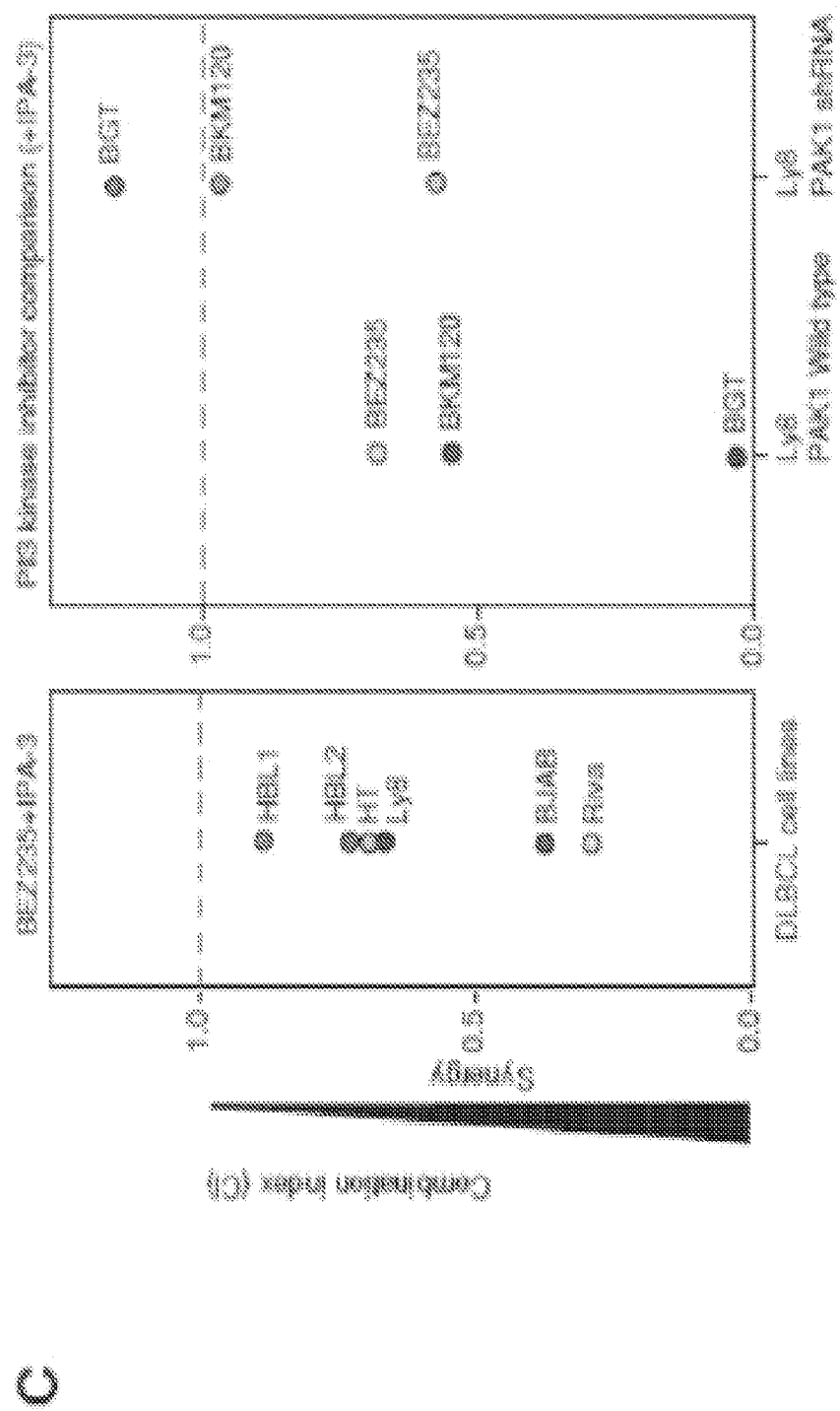

Accordingly, RNA interference was used to knock down expression of the PAK1 gene. Lentiviral vectors delivered three separate short-hairpin RNA (shRNA) constructs directed against PAK1 in the Ly8 cell line, which normally exhibits robust PAK1 expression and relative resistance to PI3K inhibition. Those experiments yielded three separate cell lines with stable knockdown of PAK1 expression, characterized by reduced PAK1 protein and mRNA expression. FIG. 5A, left panel, depicts the reduction in PAK1 protein expression observed for each of those three cell lines compared with the parental, unmodified Ly8 cells. Those three PAK1-knockdown cell lines were then tested to compare their sensitivity to PI3K inhibition with that of unmodified Ly8 cells. Reduced PAK1 expression in the modified cells led to significantly decreased resistance to PI3K inhibition. FIG. 5A, middle panel, shows an exemplary MTT assay for the cell line expressing PAK1 shRNA #3 treated with BEZ235; the shRNA expressing cells showed a significant decrease in the proportion of viable cells observed compared with unmodified Ly8 cells (P<0.01). The right panel of FIG. 5A shows that the three shRNA-modified cell lines were, on average, 3.5-fold more sensitive to the effects of BEZ235 than unmodified Ly8 cells, a statistically significant difference (P<0.01).

Small-molecule inhibition of PAK1 with IPA-3 achieved consistent results. PAK1 inhibition with IPA-3 was tested in nine different cells lines, both individually and in combination with BEZ235. As a single agent, IPA-3 had limited effectiveness at therapeutically achievable concentrations, with observed IC50 values ranging from 0.697 μmol/L to no cell death at 10 μmol/L. In contrast, even in cell lines that were relatively resistant to the effects of IPA-3 as a single agent, PAK1 inhibition with IPA-3 conferred increased sensitivity to BEZ235. As shown in the top two panels of FIG. 5B, treatment of BJAB cells separately with IPA-3 alone and BEZ235 alone as well as simultaneously with both drugs showed that concurrent treatment with IPA-3 and BEZ235 was much more effective than treatment with either drug alone. Similarly, the bottom two panels of FIG. 5B show that separate or simultaneous treatment of Ly8 cells with the two drugs followed the same pattern, with the combination of drugs providing increased effectiveness.

The combination of BEZ235 and IPA-3 was tested in five different cell lines predicted to be resistant to BEZ235 (HBL1, HBL2, HT, Ly8, and Riva). In each case, inhibition of PAK1 greatly potentiated the effects of PI3K inhibition. The Chou-Talalay method was used to identify synergy between the two agents in those five cell lines, and all five lines showed synergy in cell killing between the PI3K and PAK1 inhibitors (P<0.01), with a synergy combination index ranging from 0.3 to 0.86 (FIG. 5C, left panel). In addition, the three separate PI3K inhibitors were also tested in combination with IPA-3 in Ly8 cells with and without shRNA-mediated knockdown of PAK1. In the context of shRNA-mediated PAK1 knockdown, there was a substantial decrease in the synergy between PAK1 and each of the three PI3K inhibitors, while all three PI3K inhibitors exhibited synergy with PAK1 in Ly8 cells without the shRNA knockdown (FIG. 5C, right panel). Those data suggest that the observed synergism between PI3K inhibitors and IPA-3 depends on PAK1 expression and that PAK1 inhibition can overcome resistance to PI3K inhibition.

Figure 6:
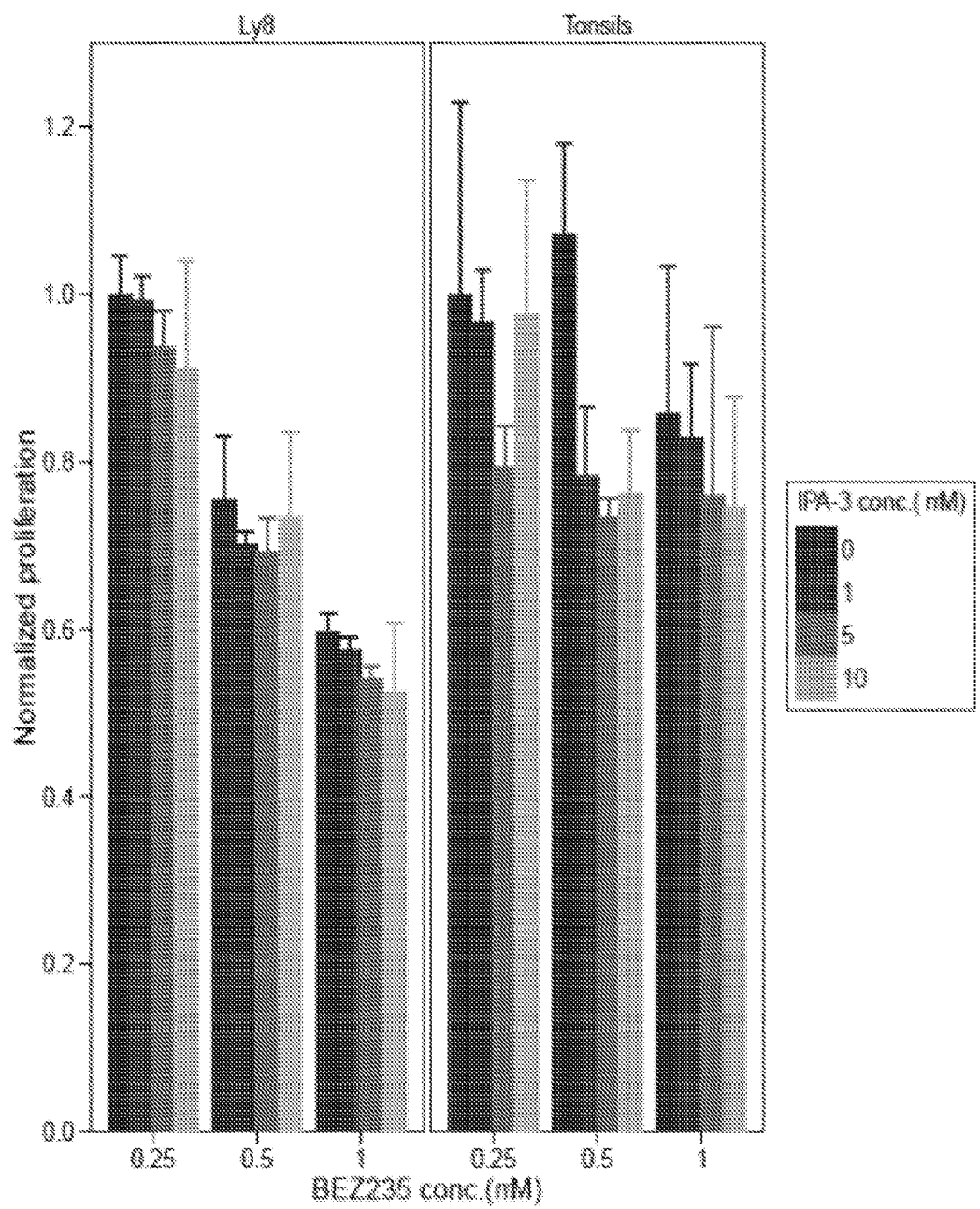
FIG. 6 shows that the combination of PAK1 inhibition and PI3K inhibition is selectively toxic to B-cell lymphoma cells (Ly8) compared with normal B cells derived from tonsil tissue.

Finally, BEZ235 and IPA-3 were administered separately and concurrently to normal human B cells to ascertain a therapeutic window between normal and malignant cells. As shown in FIG. 6, the drugs showed selective toxicity, both alone and in combination, in Ly8 cells as compared to normal B cells.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

We claim:

1. A method for treating a blood cancer in a subject, comprising administering a PI3K inhibitor to a subject having a blood cancer wherein the level of PAK1 expression in a sample from the subject is below a control.

2. The method of claim 1, wherein the control is about 256 arbitrary units.

3. The method of claim 1, wherein the blood cancer is a lymphoma.

4. The method of claim 3, wherein the lymphoma is a B-cell lymphoma.

5. The method of claim 1, wherein the PI3K inhibitor also inhibits mTOR.

6. A method for determining resistance of a blood cancer to a PI3K inhibitor, comprising measuring a level of PAK1 expression in a sample comprising malignant cells from a subject having blood cancer, wherein PAK1 expression above a control indicates resistance of the blood cancer to the PI3K inhibitor.

7. The method of claim 6, wherein the control is about 256 arbitrary units.

8. The method of claim 6, wherein the blood cancer is a lymphoma.

9. The method of claim 8, wherein the lymphoma is a B-cell lymphoma.

10. The method of claim 6, further comprising treating the sample to create a test material and exposing the test material to a probe configured to detect PAK1 expression in the test material.

11. The method of claim 10, wherein the probe comprises an antibody.

12. The method of claim 8, wherein the probe comprises a nucleic acid.

13. A method for treating a blood cancer in a subject, comprising administering a PI3K inhibitor and a PAK1 inhibitor to a subject having a blood cancer, wherein the level of PAK1 expression in the sample is above a control.

14. The method of claim 13, wherein the control is about 256 arbitrary units.

15. The method of claim 13, wherein the blood cancer is a lymphoma.

16. The method of claim 15, wherein the lymphoma is a B-cell lymphoma.

17. The method of claim 13, wherein the PI3K inhibitor also inhibits mTOR.

18. A method for treating a blood cancer in a subject, comprising (a) requesting a test to determine a level of PAK1 expression in a sample from a subject having blood cancer and obtaining results of the test, and (b) if the results of the test indicate that the level of PAK1 expression in the sample from the subject is below a control, administering a PI3K inhibitor to the subject.

19. A method for treating a blood cancer in a subject, comprising (a) requesting a test to determine a level of PAK1 expression in a sample from the subject and obtaining the results of the test, and (b) if the results of the test indicate that the level of PAK1 expression in the sample from the subject is above a control, administering a PI3K inhibitor and a PAK1 inhibitor to the subject.

20. A method for treating a blood cancer in a subject, comprising administering to the subject a PI3K inhibitor and IPA-3.

21. The method of claim 20, wherein the blood cancer is a lymphoma.

22. The method of claim 21, wherein the lymphoma is a B-cell lymphoma.

23. The method of claim 20, wherein the PI3K inhibitor also inhibits mTOR.

* * * * *

SEQUENCE LISTING

<160> NUMBER OF SEQ ID NOS: 24

<210> SEQ ID NO 1
<211> LENGTH: 40
<212> TYPE: DNA
<213> ORGANISM: Artificial Sequence
<220> FEATURE:
<223> OTHER INFORMATION: Primer

<400> SEQUENCE: 1
acactctttc cctacacgac gctcttccga tctgcctaat                                40

<210> SEQ ID NO 2
<211> LENGTH: 39
<212> TYPE: DNA

```
<213> ORGANISM: Artificial Sequence
<220> FEATURE:
<223> OTHER INFORMATION: Primer

<400> SEQUENCE: 2
ttaggcagat cggaagagcg tcgtgtaggg aaagagtgt                    39

<210> SEQ ID NO 3
<211> LENGTH: 6
<212> TYPE: DNA
<213> ORGANISM: Artificial Sequence
<220> FEATURE:
<223> OTHER INFORMATION: Primer

<400> SEQUENCE: 3 gcctaa                                                        6

<210> SEQ ID NO 4
<211> LENGTH: 40
<212> TYPE: DNA
<213> ORGANISM: Artificial Sequence
<220> FEATURE:
<223> OTHER INFORMATION: Primer

<400> SEQUENCE: 4
acactctttc cctacacgac gctcttccga tctgtagcct                   40

<210> SEQ ID NO 5
<211> LENGTH: 39
<212> TYPE: DNA
<213> ORGANISM: Artificial Sequence
<220> FEATURE:
<223> OTHER INFORMATION: Primer

<400> SEQUENCE: 5
ggctacagat cggaagagcg tcgtgtaggg aaagagtgt                    39

<210> SEQ ID NO 6
<211> LENGTH: 6
<212> TYPE: DNA
<213> ORGANISM: Artificial Sequence
<220> FEATURE:
<223> OTHER INFORMATION: Primer

<400> SEQUENCE: 6 gtagcc                                                        6

<210> SEQ ID NO 7
<211> LENGTH: 40
<212> TYPE: DNA
<213> ORGANISM: Artificial Sequence
<220> FEATURE:
<223> OTHER INFORMATION: Primer

<400> SEQUENCE: 7
acactctttc cctacacgac gctcttccga tcttggtcat                   40

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
tgaccaagat cggaagagcg tcgtgtaggg aaagagtgt                    39
```

```
<210> SEQ ID NO 9
<211> LENGTH: 6
<212> TYPE: DNA
<213> ORGANISM: Artificial Sequence
<220> FEATURE:
<223> OTHER INFORMATION: Primer

<400> SEQUENCE: 9 tggtca                                                                    6

<210> SEQ ID NO 10
<211> LENGTH: 40
<212> TYPE: DNA
<213> ORGANISM: Artificial Sequence
<220> FEATURE:
<223> OTHER INFORMATION: Primer

<400> SEQUENCE: 10
acactctttc cctacacgac gctcttccga tctattggct                              40

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
gccaatagat cggaagagcg tcgtgtaggg aaagagtgt                               39

<210> SEQ ID NO 12
<211> LENGTH: 6
<212> TYPE: DNA
<213> ORGANISM: Artificial Sequence
<220> FEATURE:
<223> OTHER INFORMATION: Primer

<400> SEQUENCE: 12 attggc                                                                    6

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
acactctttc cctacacgac gctcttccga tctgatctgt                              40

<210> SEQ ID NO 14
<211> LENGTH: 39
<212> TYPE: DNA
<213> ORGANISM: Artificial Sequence
<220> FEATURE:
<223> OTHER INFORMATION: Primer

<400> SEQUENCE: 14
cagatcagat cggaagagcg tcgtgtaggg aaagagtgt                               39

<210> SEQ ID NO 15
<211> LENGTH: 6
<212> TYPE: DNA
<213> ORGANISM: Artificial Sequence
<220> FEATURE:
```

<223> OTHER INFORMATION: Primer

<400> SEQUENCE: 15 gatctg                                                                    6

<210> SEQ ID NO 16
<211> LENGTH: 40
<212> TYPE: DNA
<213> ORGANISM: Artificial Sequence
<220> FEATURE:
<223> OTHER INFORMATION: Primer

<400> SEQUENCE: 16
acactctttc cctacacgac gctcttccga tcttcaagtt                              40

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
acttgaagat cggaagagcg tcgtgtaggg aaagagtgt                               39

<210> SEQ ID NO 18
<211> LENGTH: 6
<212> TYPE: DNA
<213> ORGANISM: Artificial Sequence
<220> FEATURE:
<223> OTHER INFORMATION: Primer

<400> SEQUENCE: 18 tcaagt                                                                    6

<210> SEQ ID NO 19
<211> LENGTH: 40
<212> TYPE: DNA
<213> ORGANISM: Artificial Sequence
<220> FEATURE:
<223> OTHER INFORMATION: Primer

<400> SEQUENCE: 19
acactctttc cctacacgac gctcttccga tctctgatct                              40

<210> SEQ ID NO 20
<211> LENGTH: 39
<212> TYPE: DNA
<213> ORGANISM: Artificial Sequence
<220> FEATURE:
<223> OTHER INFORMATION: Primer

<400> SEQUENCE: 20
gatcagagat cggaagagcg tcgtgtaggg aaagagtgt                               39

<210> SEQ ID NO 21
<211> LENGTH: 6
<212> TYPE: DNA
<213> ORGANISM: Artificial Sequence
<220> FEATURE:
<223> OTHER INFORMATION: Primer

<400> SEQUENCE: 21 ctgatc                                                                    6

```
<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
acactctttc cctacacgac gctcttccga tctaagctat                              40

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
tagcttagat cggaagagcg tcgtgtaggg aaagagtgt                               39

<210> SEQ ID NO 24
<211> LENGTH: 6
<212> TYPE: DNA
<213> ORGANISM: Artificial Sequence
<220> FEATURE:
<223> OTHER INFORMATION: Primer

<400> SEQUENCE: 24 aagcta                                                                   6
```